(12) United States Patent
Reisfeld et al.

(10) Patent No.: US 8,048,428 B2
(45) Date of Patent: *Nov. 1, 2011

(54) DNA COMPOSITION ENCODING AN IMMUNOGENIC VEGF RECEPTOR PEPTIDE AND METHODS OF USE THEREOF

(75) Inventors: Ralph A. Reisfeld, La Jolla, CA (US); Andreas G. Niethammer, Heidelberg (DE); Rong Xiang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 1467 days.

This patent is subject to a terminal disclaimer.

(21) Appl. No.: 11/507,298

(22) Filed: Aug. 21, 2006

(65) Prior Publication Data

US 2007/0059323 A1    Mar. 15, 2007

Related U.S. Application Data

(63) Continuation-in-part of application No. 10/090,183, filed on Mar. 2, 2002, now Pat. No. 7,094,410.

(51) Int. Cl.
*A61K 39/00* (2006.01)
*A61K 48/00* (2006.01)
*C12N 1/21* (2006.01)
*A01N 63/00* (2006.01)

(52) U.S. Cl. .............. 424/200.1; 424/185.1; 424/93.2; 424/93.4; 435/252.3

(58) Field of Classification Search .................. None
See application file for complete search history.

(56) References Cited

U.S. PATENT DOCUMENTS
2007/0059323 A1* 3/2007 Reisfeld et al. ........... 424/200.1

FOREIGN PATENT DOCUMENTS
WO     WO 99/45018      9/1999

OTHER PUBLICATIONS

Kuo, C.J. et al., "Comparative evaluation of the antitumor activity of antiangiogenic proteins delivered by gene transfer", Apr. 2001 (online Mar. 27, 2001), PNAS, vol. 98: pp. 4605-4610.*

* cited by examiner

*Primary Examiner* — Michael Burkhart
(74) *Attorney, Agent, or Firm* — Olson & Cepuritis, Ltd.

(57) ABSTRACT

A DNA composition effective for inhibiting endothelial cell proliferation comprises a DNA construct operably encoding a vascular endothelial growth factor (VEGF) receptor polypeptide, which can be a full length VEGF receptor protein or an immunogenic fragment thereof. This invention provides DNA compositions that encode VEGF receptor-2 (KDR), VEGF receptor-1 (Flt-1), or Flk-1 (the murine homolog of KDR), as well as methods of using such a DNA composition to inhibit vascular endothelial cell proliferation in the tumor micro-environment. Angiogenesis inhibition and subsequent decrease in tumor growth and dissemination is achieved.

7 Claims, 20 Drawing Sheets

FIGURE 1

Human KDR, DNA, codons 1 - 4071

SEQ. ID NO.: 1.

| | | | | | |
|---|---|---|---|---|---:|
| atggagagca | aggtgctgct | ggccgtcgcc | ctgtggctct | gcgtggagac | ccgggccgcc | 60 |
| tctgtgggtt | tgcctagtgt | ttctcttgat | ctgcccaggc | tcagcataca | aaaagacata | 120 |
| cttacaatta | aggctaatac | aactcttcaa | attacttgca | ggggacagag | ggacttggac | 180 |
| tggctttggc | ccaataatca | gagtggcagt | gagcaaaggg | tggaggtgac | tgagtgcagc | 240 |
| gatggcctct | tctgtaagac | actcacaatt | ccaaaagtga | tcggaaatga | cactggagcc | 300 |
| tacaagtgct | tctaccggga | aactgacttg | gcctcggtca | tttatgtcta | tgttcaagat | 360 |
| tacagatctc | catttattgc | ttctgttagt | gaccaacatg | gagtcgtgta | cattactgag | 420 |
| aacaaaaaca | aaactgtggt | gattccatgt | ctcgggtcca | tttcaaatct | caacgtgtca | 480 |
| ctttgtgcaa | gatacccaga | aaagagattt | gttcctgatg | taacagaat | tcctgggac | 540 |
| agcaagaagg | gctttactat | tcccagctac | atgatcagct | atgctggcat | ggtcttctgt | 600 |
| gaagcaaaaa | ttaatgatga | agttaccag | tctattatgt | acatagttgt | cgttgtaggg | 660 |
| tataggattt | atgatgtggt | tctgagtccg | tctcatggaa | ttgaactatc | tgttggagaa | 720 |
| aagcttgtct | taaattgtac | agcaagaact | gaactaaatg | tggggattga | cttcaactgg | 780 |
| gaataccctt | cttcgaagca | tcagcataag | aaacttgtaa | accgagacct | aaaaacccag | 840 |
| tctgggagtg | agatgaagaa | atttttgagc | accttaacta | tagatggtgt | aacccggagt | 900 |
| gaccaaggat | tgtacacctg | tgcagcatcc | agtgggctga | tgaccaagaa | gaacagcaca | 960 |
| tttgtcaggg | tccatgaaaa | accttttgtt | gcttttggaa | gtggcatgga | atctctggtg | 1020 |
| gaagccacgg | tgggggagcg | tgtcagaatc | cctgcgaagt | accttggtta | cccaccccca | 1080 |
| gaaataaaat | ggtataaaaa | tggaataccc | cttgagtcca | atcacacaat | taaagcgggg | 1140 |
| catgtactga | cgattatgga | agtgagtgaa | agagacacag | gaaattacac | tgtcatcctt | 1200 |
| accaatccca | tttcaaagga | gaagcagagc | catgtggtct | ctctggttgt | gtatgtccca | 1260 |
| ccccagattg | tgagaaatc | tctaatctct | cctgtggatt | cctaccagta | cggcaccact | 1320 |
| caaacgctga | catgtacggt | ctatgccatt | cctccccgc | atcacatcca | ctggtattgg | 1380 |
| cagttggagg | aagagtgcgc | aacgagccc | agccaagctg | tctcagtgac | aaacccatac | 1440 |
| ccttgtgaag | aatggagaag | tgtggaggac | ttccaggag | aaataaaat | tgaagttaat | 1500 |
| aaaaatcaat | ttgctctaat | tgaaggaaaa | aacaaaactg | taagtaccct | tgttatccaa | 1560 |
| gcggcaaatg | tgtcagcttt | gtacaaatgt | gaagcggtca | caaagtcgg | agaggagag | 1620 |
| agggtgatct | ccttccacgt | gaccagggt | cctgaaatta | ctttgcaacc | tgacatgcag | 1680 |
| cccactgagc | aggagagcgt | gtctttgtgg | tgcactgcag | acagatctac | gtttgagaac | 1740 |
| ctcacatggt | acaagcttgg | cccacagcct | ctgccaatcc | atgtgggaga | gttgcccaca | 1800 |
| cctgtttgca | gaacttgga | tactctttgg | aaattgaatg | ccaccatgtt | ctctaatagc | 1860 |
| acaaatgaca | ttttgatcat | ggagcttaag | aatgcatcct | tgcaggacca | aggagactat | 1920 |
| gtctgccttg | ctcaagacag | gaagaccaag | aaaagacatt | gcgtggtcag | gcagctcaca | 1980 |
| gtcctagagc | gtgtggcacc | cacgatcaca | ggaaacctgg | agaatcagac | gacaagtatt | 2040 |
| ggggaaagca | tcgaagtctc | atgcacggca | tctgggaatc | ccctccaca | gatcatgtgg | 2100 |
| tttaaagata | atgagaccct | tgtagaagac | tcaggcattg | tattgaagga | tgggaaccgg | 2160 |

FIGURE 1 - continued

```
aacctcacta tccgcagagt gaggaaggag gacgaaggcc tctacacctg ccaggcatgc    2220
agtgttcttg gctgtgcaaa agtggaggca ttttcataa tagaaggtgc ccaggaaaag     2280
acgaacttgg aaatcattat tctagtaggc acggcggtga ttgccatgtt cttctggcta    2340
cttcttgtca tcatcctacg gaccgttaag cgggccaatg gaggggaact gaagacaggc    2400
tacttgtcca tcgtcatgga tccagatgaa ctcccattgg atgaacattg tgaacgactg    2460
ccttatgatg ccagcaaatg ggaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820
aaagggcac gattccgtca agggaaagac tacgttggag caatccctgt ggatctgaaa     2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatatttccc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc ctcctgttta a              4071
```

FIGURE 2

Human KDR, protein
SEQ. ID NO.: 2

MQSKVLLAVALWLCVETRAASVGLPSVSLDLPRLSIQKDILTIKA
NTTLQITCRGQRDLDWLWPNNQSGSEQRVEVTECSDGLFCKTLTIPKVIGNDTGAYKCF
YRETDLASVIYVYVQDYRSPFIASVSDQHGVVYITENKNKTVVIPCLGSISNLNVSLCA
RYPEKRFVPDGNRISWDSKKGFTIPSYMISYAGMVFCEAKINDESYQSIMYIVVVVGYR
IYDVVLSPSHGIELSVGEKLVLNCTARTELNVGIDFNWEYPSSKHQHKKLVNRDLKTQS
GSEMKKFLSTLTIDGVTRSDQGLYTCAASSGLMTKKNSTFVRVHEKPFVAFGSGMESLV
EATVGERVRIPAKYLGYPPPEIKWYKNGIPLESNHTIKAGHVLTIMEVSERDTGNYTVI
LTNPISKEKQSHVVSLVVYVPPQIGEKSLISPVDSYQYGTTQTLTCTVYAIPPPHHIHW
YWQLEEECANEPSQAVSVTNPYPCEEWRSVEDFQGGNKIEVNKQFALIEGKNKTVSTL
VIQAANVSALYKCEAVNKVGRGERVISFHVTRGPEITLQPDMQPTEQESVSLWCTADRS
TFENLTWYKLGPQPLPIHVGELPTPVCKNLDTLWKLNATMFSNSTNDILIMELKNASLQ
DQGDYVCLAQDRKTKKRHCVVRQLTVLERVAPTITGNLENQTTSIGESIEVSCTASGNP
PPQIMWFKDNETLVEDSGIVLKDGNRNLTIRRVRKEDEGLYTCQACSVLGCAKVEAFFI
IEGAQEKTNLEIIILVGTAVIAMFFWLLLVIILRTVKRANGGELKTGYLSIVMDPDELP
LDEHCERLPYDASKWEFPRDRLKLGKPLGRGAFGQVIEADAFGIDKTATCRTVAVKMLK
EGATHSEHRALMSELKILIHIGHHLNVVNLLGACTKPGGPLMVIVEFCKFGNLSTYLRS
KRNEFVPYKTKGARFRQGKDYVGAIPVDLKRRLDSITSSQSSASSGFVEEKSLSDVEEE
EAPEDLYKDFLTLEHLICYSFQVAKGMEFLASRKCIHRDLAARNILLSEKNVVKICDFG
LARDIYKDPDYVRKGDARLPLKWMAPETIFDRVYTIQSDVWSFGVLLWEIFSLGASPYP
GVKIDEEFCRRLKEGTRMRAPDYTTPEMYQTMLDCWHGEPSQRPTFSELVEHLGNLLQA
NAQQDGKDYIVLPISETLSMEEDSGLSLPTSPVSCMEEEEVCDPKFHYDNTAGISQYLQ
NSKRKSRPVSVKTFEDIPLEEPEVKVIPDDNQTDSGMVLASEELKTLEDRTKLSPSFGG
MVPSKSRESVASEGSNQTSGYQSGYHSDDTDTTVYSSEEAELLKLIEIGVQTGSTAQIL
QPDSGTTLSSPPV

FIGURE 3

Human Flt-1, DNA, codons 1 - 4017
SEQ. ID NO.: 3

```
    atggtcagct actgggacac cggggtcctg ctgtgcgcgc tgctcagctg tctgcttctc     60
    acaggatcta gttcaggttc aaaattaaaa gatcctgaac tgagtttaaa aggcacccag    120
    cacatcatgc aagcaggcca gacactgcat ctccaatgca ggggggaagc agcccataaa    180
    tggtctttgc ctgaaatggt gagtaaggaa agcgaaaggc tgagcataac taaatctgcc    240
    tgtggaagaa atggcaaaca attctgcagt actttaacct tgaacacagc tcaagcaaac    300
    cacactggct ctacagctg caaatatcta gctgtaccta cttcaaagaa gaaggaaaca    360
    gaatctgcaa tctatatatt tattagtgat acaggtagac tttcgtaga gatgtacagt    420
    gaaatcccg aaattataca catgactgaa ggaagggagc tcgtcattcc ctgccgggtt    480
    acgtcaccta acatcactgt tactttaaaa aagtttccac ttgacacttt gatccctgat    540
    ggaaaacgca taatctggga cagtagaaag ggcttcatca tatcaaatgc aacgtacaaa    600
    gaaatagggc ttctgacctg tgaagcaaca gtcaatgggc atttgtataa gacaaactat    660
    ctcacacatc gacaaaccaa tacaatcata gatgtccaaa taagcacacc acgcccagtc    720
    aaattactta gaggccatac tcttgtcctc aattgtactg ctaccactcc cttgaacacg    780
    agagttcaaa tgacctggag ttaccctgat gaaaaaaata gagagcttc cgtaaggcga    840
    cgaattgacc aaagcaattc ccatgccaac atattctaca gtgttcttac tattgacaaa    900
    atgcagaaca agacaaagg actttatact tgtcgtgtaa ggagtggacc atcattcaaa    960
    tctgttaaca cctcagtgca tatatatgat aaagcattca tcactgtgaa acatcgaaaa   1020
    cagcaggtgc ttgaaaccgt agctggcaag cggtcttacc ggctctctat gaaagtgaag   1080
    gcatttcct cgccggaagt tgtatggtta aaagatgggt acctgcgac tgagaaatct   1140
    gctcgctatt tgactcgtgg ctactcgtta attatcaagg acgtaactga agaggatgca   1200
    gggaattata caatcttgct gagcataaaa cagtcaaatg tgtttaaaaa cctcactgcc   1260
    actctaattg tcaatgtgaa accccagatt tacgaaaagg ccgtgtcatc gtttccagac   1320
    ccggctctct acccactggg cagcagacaa atcctgactt gtaccgcata tggtatccct   1380
    caacctacaa tcaagtggtt ctggcacccc tgtaaccata atcattccga agcaaggtgt   1440
    gacttttgtt ccaataatga agagtccttt atcctggatg ctgacagcaa catgggaaac   1500
    agaattgaga gcatcactca gcgcatggca ataatagaag gaaagaataa gatggctagc   1560
    accttggttg tggctgactc tagaatttct ggaatctaca tttgcatagc ttccaataaa   1620
    gttgggactg tgggaagaaa cataagcttt tatatcacag atgtgccaaa tgggtttcat   1680
    gttaacttgg aaaaaatgcc gacggaagga gaggacctga aactgtcttg cacagttaac   1740
    aagttcttat acagagacgt tacttggatt ttactgcgga cagtaataa cagaacaatg   1800
    cactacagta ttagcaagca aaaatggcc atcactaagg agcactccat cactcttaat   1860
    cttaccatca tgaatgtttc cctgcaagat tcaggcacct atgcctgcag agccaggaat   1920
    gtatacacag gggaagaaat cctccagaag aaagaaatta atcagaga tcaggaagca   1980
    ccatacctcc tgcgaaacct cagtgatcac acagtggcca tcagcagttc caccacttta   2040
    gactgtcatg ctaatggtgt ccccgagcct cagatcactt ggtttaaaaa caaccacaaa   2100
    atacaacaag agcctggaat tatttaga ccaggaagca gcacgctgtt tattgaaaga   2160
```

FIGURE 3 - continued

```
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaaggtcttc ttctgaaata aagactgact acctatcaat tataatggac    2400
ccagatgaag ttcctttgga tgagcagtgt gagcggctcc cttatgatgc cagcaagtgg    2460
gagtttgccc gggagagact taaactgggc aaatcacttg aagaggggc ttttggaaaa     2520
gtggttcaag catcagcatt tggcattaag aaatcaccta cgtgccggac tgtggctgtg    2580
aaaatgctga agagggggc cacggccagc gagtacaaag ctctgatgac tgagctaaaa     2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca acgtgacttt attttttctc aacaaggatg cagcactaca catggagcct    2820
aagaaagaaa aaatggagcc aggcctggaa caaggcaaga accaagact agatagcgtc     2880
accagcagcg aaagctttgc gagctccggc tttcaggaag ataaaagtct gagtgatgtt    2940
gaggaagagg aggattctga cggtttctac aaggagccca tcactatgga gatctgatt    3000
tcttacagtt ttcaagtggc cagaggcatg gagttcctgt cttccagaaa gtgcattcat    3060
cgggacctgg cagcgagaaa cattctttta tctgagaaca acgtggtgaa gatttgtgat    3120
tttggccttg cccgggatat ttataagaac cccgattatg tgagaaaagg agatactcga    3180
cttcctctga aatggatggc tcctgaatct atctttgaca aaatctacag caccaagagc    3240
gacgtgtggt cttacggagt attgctgtgg gaaatcttct ccttaggtgg gtctccatac    3300
ccaggagtac aaatggatga ggactttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc ccaatcaatg ccatactgac aggaaatagt    3540
gggtttacat actcaactcc tgccttctct gaggacttct tcaaggaaag tatttcagct    3600
ccgaagttta attcaggaag ctctgatgat gtcagatatg taaatgcttt caagttcatg    3660
agcctggaaa gaatcaaaac ctttgaagaa cttttaccga atgccacctc catgtttgat    3720
gactaccagg gcgacagcag cactctgttg gcctctccca tgctgaagcg cttcacctgg    3780
actgacagca acccaaggc ctcgctcaag attgacttga gagtaaccag taaaagtaag     3840
gagtcggggc tgtctgatgt cagcaggccc agtttctgcc attccagctg tgggcacgtc    3900
agcgaaggca agcgcaggtt cacctacgac cacgctgagc tggaaaggaa aatcgcgtgc    3960
tgctcccgc ccccagacta caactcggtg gtcctgtact ccaccccacc catctag      4017
```

FIGURE 4

Human Flt-1, protein
SEQ. ID NO.: 4

```
            MVSYWDTGVLLCALLSCLLLTGSSSGSKLKDPELSLKGTQHIMQA
GQTLHLQCRGEAAHKWSLPEMVSKESERLSITKSACGRNGKQFCSTLTLNTAQANHTGF
YSCKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYLT
HRQTNTIIDVQISTPRPVKLLRGHTLVLNCTATTPLNTRVQMTWSYPDEKNKRASVRRR
IDQSNSHANIFYSVLTIDKMQNKDKGLYTCRVSGPSFKSVNTSVHIYDKAFITVKHRK
QQVLETVAGKRSYRLSMKVKAFPSPEVVWLKDGLPATEKSARYLTRGYSLIIKDVTEED
AGNYTILLSIKQSNVFKNLTATLIVNVKPQIYEKAVSSFPDPALYPLGSRQILTCTAYG
IPQPTIKWFWHPCNHNHSEARCDFCSNNEESFILDADSNMGNRIESITQRMAIIEGKNK
MASTLVVADSRISGIYICIASNKVGTVGRNISFYITDVPNGFHVNLEKMPTEGEDKLS
CTVNKFLYRDVTWILLRTVNNRTMHYSISKQKMAITKEHSITLNLTIMNVSLQDSGTYA
CRARNVYTGEEILQKKEITIRDQEAPYLLRNLSDHTVAISSSTTLDCHANGVPEPQITW
FKNNHKIQQEPGIILGPGSSTLFIERVTEEDEGVYHCKATNQKGSVESSAYLTVQGTSD
KSNLELITLTCTCVAATLFWLLLTLFIRKMKRSSSEIKTDYLSIIMDPDEVPLDEQCER
LPYDASKWEFARERLKLGKSLGRGAFGKVVQASAFGIKKSPTCRTVAVKMLKEGATASE
YKALMTELKILTHIGHHLNVVNLLGACTKQGGPLMVIVEYCKYGNLSNYLKSKRDLFFL
NKDAALHMEPKKEKMEPGLEQGKKPRLDSVTSSESFASSGFQEDKSLSDVEEEEDSDGF
YKEPITMEDLISYSFQVARGMEFLSSRKCIHRDLAARNILLSENNVVKICDFGLARDIY
KNPDYVRKGDTRLPLKWMAPESIFDKIYSTKSDVWSYGVLLWEIFSLGGSPYPGVQMDE
DFCSRLREGMRMRAPEYSTPEIYQIMLDCWHRDPKERPRFAELVEKLGDLLQANVQQDG
KDYIPINAILTGNSGFTYSTPAFSEDFFKESISAPKFNSGSSDDVRYVNAFKFMSLERI
KTFEELLPNATSMFDDYQGDSSTLLASPMLKRFTWTDSKPKASLKIDLRVTSKSKESGL
SDVSRPSFCHSSCGHVSEGKRRFTYDHAELERKIACCSPPPDYNSVVLYSTPPI
```

FIGURE 5

Mouse Flk-1, DNA, codons 208 - 4344

SEQ. ID NO.: 5

```
ctgtgtcccg cagccggata acctggctga cccgattccg cggacaccgc tgcagccgcg 60
gctggagcca gggcgccggt gccccgcgct ctccccggtc ttgcgctgcg ggggccatac 120
cgcctctgtg acttctttgc gggccaggga cggagaagga gtctgtgcct gagaaactgg 180
gctctgtgcc caggcgcgag gtgcaggatg gagagcaagg cgctgctagc tgtcgctctg 240
tggttctgcg tggagacccg agccgcctct gtgggtttga ctggcgattt tctccatccc 300
cccaagctca gcacacagaa agacatactg acaattttgg caaatacaac ccttcagatt 360
acttgcaggg dcagcgggga cctggactgg cttgggccca atgctcagcg tgattctgag 420
gaaagggtat tggtgactga atgcggcggt ggtgacagta tcttctgcaa acactcacc 480
attcccaggg tggttggaaa tgatactgga gcctacaagt gctcgtaccg ggacgtcgac 540
atagcctcca ctgtttatgt ctatgttcga gattacagat caccattcat cgcctctgtc 600
agtgaccagc atggcatcgt gtacatcacc gagaacaaga caaaactgt ggtgatcccc 660
tgccgagggt cgatttcaaa cctcaatgtg tctctttgcg ctaggtatcc agaaaagaga 720
tttgttccgg atggaaacag aatttcctgg gacagcgaga taggctttac tctccccagt 780
tacatgatca gctatgccgg catggtcttc tgtgaggcaa agatcaatga tgaaacctat 840
cagtctatca tgtacatagt gtgggttgta ggatatagga tttatgatgt gattctgagc 900
cccccgcatg aaattgagct atctgccgga gaaaaacttg tcttaaattg tacagcgaga 960
acagagctca atgtggggct tgatttcacc tggcactctc caccttcaaa gtctcatcat 1020
aagaagattg taaaccggga tgtgaaaccc tttcctggga ctgtggcgaa gatgttttg 1080
agccacttga aatagaaag tgtgaccaag agtgaccaag gggaatacac ctgtgtagcg 1140
tccagtggac ggatgatcaa gagaaataga acatttgtcc gagttcacac aaagcctttt 1200
attgctttcg gtagtgggat gaaatctttg gtggaagcca cagtgggcag tcaagtccga 1260
atccctgtga agtatctcag ttacccagct cctgatatca aatggtacag aaatggaagg 1320
cccattgagt ccaactacac aatgattgtt ggcgatgaac tcaccatcat ggaagtgact 1380
gaaagagatg caggaaacta cacggtcatc ctcaccaacc ccatttcaat ggagaaacag 1440
agccacatgg tctctctggt tgtgaatgtc ccaccccaga tcggtgagaa agccttgatc 1500
tcgcctatgg attcctacca gtatgggacc atgcagacat tgacatgcac agtctacgcc 1560
aaccctcccc tgcaccacat ccagtggtac tggcagctag aagaagcctg ctcctacaga 1620
cccggccaaa caagcccgta tgcttgtaaa gaatggagac acgtggagga tttccagggg 1680
ggaaacaaga tcgaagtcac caaaaccaa tatgccctga ttgaaggaaa aacaaaaact 1740
gtaagtacgc tggtcatcca agctgccaac gtgtcagcgt tgtacaaatg tgaagccatc 1800
aacaaagcgg gacgaggaga gagggtcatc tccttccatg tgatcagggg tcctgaaatt 1860
actgtgcaac ctgctgccca gccaactgag caggagagtg tgtccctgtt gtgcactgca 1920
gacagaaata cgtttgagaa cctcacgtgg tacaagcttg gctcacaggc aacatcggtc 1980
cacatgggcg aatcactcac accagttgc aagaacttgg atgctctttg gaaactgaat 2040
ggcaccatgt ttctaacag cacaaatgac atcttgattg tggcatttca gaatgcctct 2100
ctgcaggacc aaggcgacta tgttgctctc gctcaagata gaagaccaa gaaagacat 2160
```

FIGURE 5 - continued

```
tgcctggtca aacagctcat catcctagag cgcatggcac ccatgatcac cggaaatctg 2220
gagaatcaga caacaaccat tggcgagacc attgaagtga cttgcccagc atctggaaat 2280
cctaccccac acattacatg gttcaaagac aacgagaccc tggtagaaga ttcaggcatt 2340
gtactgagag atgggaaccg gaacctgact atccgcaggg tgaggaagga ggatggaggc 2400
ctctacacct gccaggcctg caatgtcctt ggctgtgcaa gagcggagac gctcttcata 2460
atagaaggtg cccaggaaaa gaccaacttg gaagtcatta tcctcgtcgg cactgcagtg 2520
attgccatgt tcttctggct ccttcttgtc attgtcctac ggaccgttaa gcgggccaat 2580
gaaggggaac tgaagacagg ctacttgtct attgtcatgg atccagatga attgcccttg 2640
gatgagcgct gtgaacgctt gccttatgat gccagcaagt gggaattccc cagggaccgg 2700
ctgaaactag gaaaacctct tggccgcggt gccttcggcc aagtgattga ggcagacgct 2760
tttggaattg acaagacagc gacttgcaaa acagtagccg tcaagatgtt gaaagaagga 2820
gcaacacaca gcgagcatcg agccctcatg tctgaactca agatcctcat ccacattggt 2880
caccatctca atgtggtgaa cctcctaggc gcctgcacca agccgggagg gcctctcatg 2940
gtgattgtgg aattctgcaa gtttggaaac ctatcaactt acttacgggg caagagaaat 3000
gaatttgttc cctataagag caaaggggca cgcttccgcc agggcaagga ctacgttggg 3060
gagctctccg tggatctgaa aagacgcttg gacagcatca ccagcagcca gagctctgcc 3120
agctcaggct tgttgagga gaaatcgctc agtgatgtag aggaagaaga agcttctgaa 3180
gaactgtaca aggacttcct gaccttggag catctcatct gttacagctt ccaagtggct 3240
aagggcatgg agttcttggc atcaaggaag tgtatccaca gggacctggc agcacgaaac 3300
attctcctat cggagaagaa tgtggttaag atctgtgact tcggcttggc ccgggacatt 3360
tataaagacc cggattatgt cagaaaagga gatgcccgac tccctttgaa gtggatggcc 3420
ccggaaacca tttttgacag agtatacaca attcagagcg atgtgtggtc tttcggtgtg 3480
ttgctctggg aaatattttc cttaggtgcc tccccatacc ctggggtcaa gattgatgaa 3540
gaattttgta ggagattgaa agaaggaact agaatgcggg ctcctgacta cactacccca 3600
gaaatgtacc agaccatgct ggactgctgg catgaggacc ccaaccagag accctcgttt 3660
tcagagttgg tggagcattt gggaaacctc tgcaagcaa atgcgcagca ggatggcaaa 3720
gactatattg ttcttccaat gtcagagaca ctgagcatgg aagaggattc tggactctcc 3780
ctgcctacct cacctgtttc ctgtatggag aagaggaag tgtgcgaccc caaattccat 3840
tatgacaaca cagcaggaat cagtcattat ctccagaaca gtaagcgaaa gagccggcca 3900
gtgagtgtaa aaacatttga agatatccca ttggaggaac cagaagtaaa agtgatccca 3960
gatgacagcc agacagacag tgggatggtc cttgcatcag aagagctgaa aactctggaa 4020
gacaggaaca aattatctcc atcttttggt ggaatgatgc cagtaaaag cagggagtct 4080
gtggcctcgg aaggctccaa ccagaccagt ggctaccagt ctgggtatca ctcagatgac 4140
acagacacca ccgtgtactc cagcgacgag gcaggacttt taaagatggt ggatgctgca 4200
gttcacgctg actcagggac cacactgcgc tcacctcctg tttaaatgga agtggtcctg 4260
tcccggctcc gcccccaact cctggaaatc acgagagagg tgctgcttag attttcaagt 4320
gttgttcttt ccaccacccg gaagtagcca catttgattt tcatttttgg aggagggacc 4380
tcagactgca aggagcttgt cctcagggca tttccagaga agatgcccat gacccaagaa 4440
tgtgttgact ctactctctt ttccattcat ttaaaagtcc tatataatgt gccctgctgt 4500
```

FIGURE 5 - continued

```
ggtctcacta ccagttaaag caaaagactt tcaaacacgt ggactctgtc ctccaagaag 4560
tggcaacggc acctctgtga aactggatcg aatgggcaat gctttgtgtg ttgaggatgg 4620
gtgagatgtc ccagggccga gtctgtctac cttggaggct tgtggagga tgcggctatg 4680
agccaagtgt taagtgtggg atgtggactg ggaggaagga aggcgcaagt cgctcggaga 4740
gcggttggag cctgcagatg cattgtgctg gctctggtgg aggtgggctt gtggcctgtc 4800
aggaaacgca aaggcggccg gcagggtttg gttttggaag gtttgcgtgc tcttcacagt 4860
cgggttacag gcgagttccc tgtggcgttt cctactccta atgagagttc cttccggact 4920
cttacgtgtc tcctggcctg gccccaggaa ggaaatgatg cagcttgctc cttcctcatc 4980
tctcaggctg tgccttaatt cagaacacca aaagagagga acgtcggcag aggctcctga 5040
cggggccgaa gaattgtgag aacagaacag aaactcaggg tttctgctgg gtggagaccc 5100
acgtggcgcc ctggtggcag gtctgagggt tctctgtcaa gtggcggtaa aggctcaggc 5160
tggtgttctt cctctatctc cactcctgtc aggcccccaa gtcctcagta ttttagcttt 5220
gtggcttcct gatggcagaa aaatcttaat tggttggttt gctctccaga taatcactag 5280
ccagatttcg aaattacttt ttagccgagg ttatgataac atctactgta tcctttagaa 5340
ttttaaccta taaaactatg tctactggtt tctgcctgtg tgcttatgtt           5390
```

FIGURE 6

Mouse Flk-1, protein
SEQ. ID NO.: 6

MESKALLAVALWFCVETRAASVGLTGDFLHPPKLSTQKDILTILA
NTTLQITCRGQRDLDWLWPNAQRDSEERVLVTECGGGDSIFCKTLTIPRVVGNDTGAYK
CSYRDVDIASTVYVYVRDYRSPFIASVSDQHGIVYITENKNKTVVIPCRGSISNLNVSL
CARYPEKRFVPDGNRISWDSEIGFTLPSYMISYAGMVFCEAKINDETYQSIMYIVVVVG
YRIYDVILSPPHEIELSAGEKLVLNCTARTELNVGLDFTWHSPPSKSHHKKIVNRDVKP
FPGTVAKMFLSTLTIESVTKSDQGEYTCVASSGRMIKRNRTFVRVHTKPFIAFGSGMKS
LVEATVGSQVRIPVKYLSYPAPDIKWYRNGRPIESNYTMIVGDELTIMEVTERDAGNYT
VILTNPISMEKQSHMVSLVVNVPPQIGEKALISPMDSYQYGTMQTLTCTVYANPPLHHI
QWYWQLEEACSYRPGQTSPYACKEWRHVEDFQGGNKIEVTKNQYALIEGKNKTVSTLVI
QAANVSALYKCEAINKAGRGERVISFHVIRGPEITVQPAAQPTEQESVSLLCTADRNTF
ENLTWYKLGSQATSVHMGESLTPVCKNLDALWKLNGTMFSNSTNDILIVAFQNASLQDQ
GDYVCSAQDKKTKKRHCLVKQLIILERMAPMITGNLENQTTTIGETIEVTCPASGNPTP
HITWFKDNETLVEDSGIVLRDGNRNLTIRRVRKEDGGLYTCQACNVLGCARAETLFIIE
GAQEKTNLEVIILVGTAVIAMFFWLLLVIVLRTVKRANEGELKTGYLSIVMDPDELPLD
ERCERLPYDASKWEFPRDRLKLGKPLGRGAFGQVIEADAFGIDKTATCKTVAVKMLKEG
ATHSEHRALMSELKILIHIGHHLNVVNLLGACTKPGGPLMVIVEFCKFGNLSTYLRGKR
NEFVPYKSKGARFRQGKDYVGELSVDLKRRLDSITSSQSSASSGFVEEKSLSDVEEEEA
SEELYKDFLTLEHLICYSFQVAKGMEFLASRKCIHRDLAARNILLSEKNVVKICDFGLA
RDIYKDPDYVRKGDARLPLKWMAPETIFDRVYTIQSDVWSFGVLLWEIFSLGASPYPGV
KIDEEFCRRLKEGTRMRAPDYTTPEMYQTMLDCWHEDPNQRPSFSELVEHLGNLLQANA
QQDGKDYIVLPMSETLSMEEDSGLSLPTSPVSCMEEEEVCDPKFHYDNTAGISHYLQNS
KRKSRPVSVKTFEDIPLEEPEVKVIPDDSQTDSGMVLASEELKTLEDRNKLSPSFGGMM
PSKSRESVASEGSNQTSGYQSGYHSDDTDTTVYSSDEAGLLKMVDAAVHADSGTTLASP
PV

A
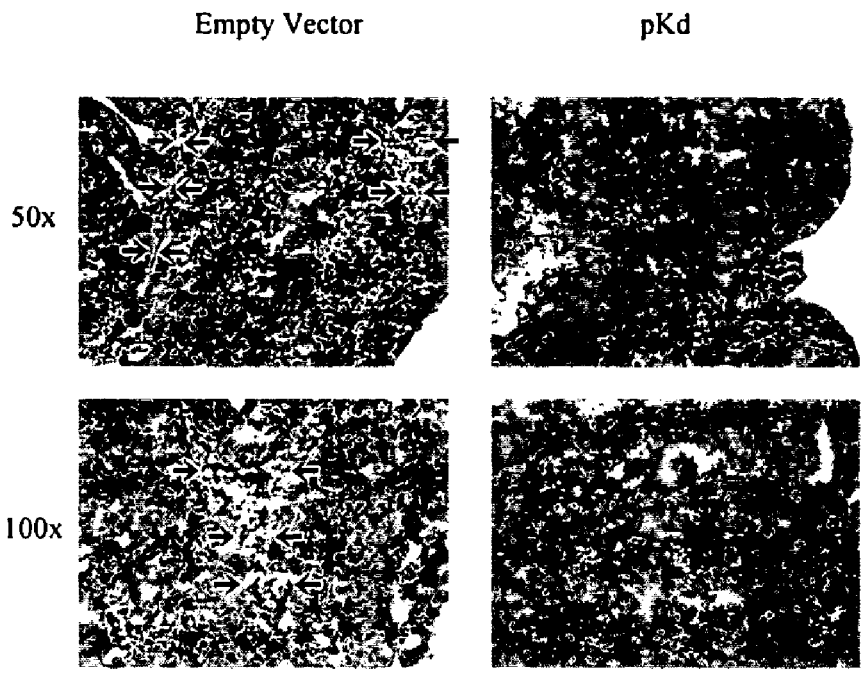
B
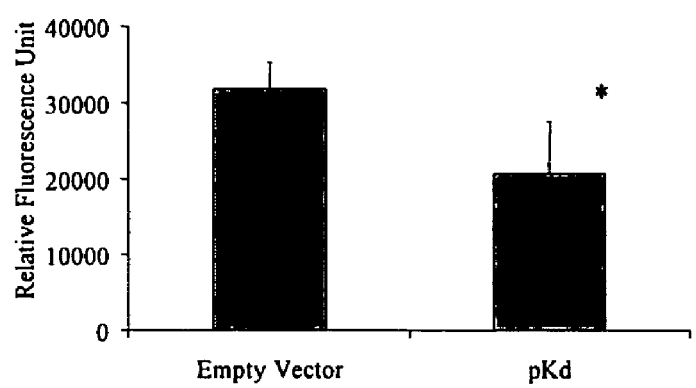
Figure 16

DNA COMPOSITION ENCODING AN IMMUNOGENIC VEGF RECEPTOR PEPTIDE AND METHODS OF USE THEREOF

CROSS-REFERENCE TO RELATED APPLICATIONS

This is a continuation-in-part of U.S. application Ser. No. 10/090,183, filed on Mar. 2, 2002, now U.S. Pat. No. 7,094,410, which is incorporated herein by reference.

GOVERNMENTAL RIGHTS

A portion of the work described herein was supported by grant numbers 5-70373-COLON, CA83856, and CA11571-A1 from the National Institutes of Health, as well as grant numbers DAMD17-02-01-0137 and DAMD17-02-01-0562 from the Department of defense. The United States Government has certain rights in this invention.

FIELD OF THE INVENTION

This invention relates to deoxyribonucleic acid (DNA) compositions encoding peptides effective for eliciting an immune response against proliferating endothelial cells. More particularly this invention relates to DNA compositions encoding for an immunogenic vascular endothelial growth factor (VEGF) receptor or an immunogenic fragment thereof. This invention also relates to methods of using the DNA composition to inhibit vascular endothelial cell proliferation, tumor growth, and angiogenesis.

BACKGROUND OF THE INVENTION

Vaccines have been utilized to provide a long term protection against a number of disease conditions by very limited administration of a prophylactic agent that stimulates an organism's immune system to destroy disease pathogens before they can proliferate and cause a pathological effect. Various approaches to vaccines and vaccinations are described in Bernard R. Glick and Jack J. Pasternak, *Molecular Biotechnology, Principles and Applications of Recombinant DNA*, Second Edition, ASM Press pp. 253-276 (1998).

Vaccination is a means of inducing the body's own immune system to seek out and destroy an infecting agent before it causes a pathological response. Typically, vaccines are either live, but attenuated, infectious agents (virus or bacteria) or a killed form of the agent. A vaccine consisting of a live bacteria or virus must be non-pathogenic. Typically, a bacterial or viral culture is attenuated (weakened) by physical or chemical treatment. Although the agent is nonvirulent, it can still elicit an immune response in a subject treated with the vaccine.

An immune response is elicited by antigens, either specific macromolecules, or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce proteins called antibodies (Ab), which selectively bind to the antigens present on the infectious agent, thus neutralizing or inactivating the pathogen (humoral immunity). In some cases, B cell response requires the assistance of CD4 helper T cells.

The specialized T cell clone that forms in response to the antigen exposure is a cytotoxic T lymphocyte (CTL), which is capable of binding to and eliminating pathogens and tissues that present the antigen (cell-mediated or cellular immunity). In some cases, an antigen presenting cell (APC) such as a dendritic cell, will envelop a pathogen or other foreign cell by endocytosis. The APC then processes the antigens from the cells, and presents these antigens in the form of a histocompatibility molecule:peptide complex to the T cell receptor (TCR) on CTLs, thus stimulating an immune response.

Humoral immunity characterized by the formation of specific antibodies is generally most effective against acute bacterial infections and repeat infections from viruses, whereas cell-mediated immunity is most effective against viral infection, chronic intracellular bacterial infection, and fungal infection. Cellular immunity is also known to protect against cancers and is responsible for rejection of organ transplants.

Antibodies to antigens from prior infections remain detectable in the blood for very long periods of time, thus affording a means of determining prior exposure to a pathogen. Upon re-exposure to the same pathogen, the immune system effectively prevents reinfection by eliminating the pathogenic agent before it can proliferate and produce a pathogenic response.

The same immune response that would be elicited by a pathogen can also sometimes be produced by a non-pathogenic agent that presents the same antigen as the pathogen. In this manner, the subject can be protected against subsequent exposure to the pathogen without having previously fought off an infection.

Not all infectious agents can be readily cultured and inactivated, as is required for vaccine formation, however. Modern recombinant DNA techniques have allowed the engineering of new vaccines to seek to overcome this limitation. Infectious agents can be created that lack the pathogenic genes, thus allowing a live, nonvirulent form of the organism to be used as a vaccine. It is also possible to engineer a relatively nonpathogenic organism such as *E. coli* to present the cell surface antigens of a pathogenic carrier. The immune system of a subject treated with such a transformed carrier is "tricked" into forming antibodies to the pathogen. The antigenic proteins of a pathogenic agent can be engineered and expressed in a nonpathogenic species and the antigenic proteins can be isolated and purified to produce a "subunit vaccine." Subunit vaccines have the advantage of being stable, safe, and chemically well defined; however, their production can be cost prohibitive.

A new approach to immunization has emerged in recent years, broadly termed genetic immunization. In this approach, a gene encoding an antigen of a pathogenic agent is operably inserted into cells in the subject to be immunized. The treated cells are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

DNA compositions encoding antigens can be introduced into the host cells of the subject by a variety of expression systems. These expression systems include prokaryotic, mammalian, and yeast expression systems. For example, one approach is to utilize a viral vector, such as vaccinia virus incorporating the new genetic material, to innoculate the host cells. Alternatively, the genetic material can be incorporated in a vector or can be delivered directly to the host cells as a "naked" polynucleotide, i.e. simply as purified DNA. In addition, the DNA can be stably transfected into attenuated bacteria such as *Salmonella typhimurium*. When a patient is orally vaccinated with the transformed *Salmonella*, the bacteria are transported to Peyer's patches in the gut (i.e., secondary lymphoid tissues), which then stimulate an immune response.

DNA compositions encoding antigens provide an opportunity to immunize against disease states that are not caused by traditional pathogens, such as genetic diseases and cancer. Typically, in a genetic cancer vaccine, antigens to a specific type of tumor cell must be isolated and then introduced into the vaccine. An effective general vaccine against a number of cancers can thus entail development of numerous individual vaccines for each type of cancer cell to be immunized against.

One general approach to treatment of tumors involves administering angiogenesis inhibiting compounds to patients with growing tumors. Angiogenesis is the process by which new capillaries and blood vessels form. Angiogenesis is important in embryonic development, tissue growth, tissue repair, and tissue regeneration. In addition to these normal and essential processes, angiogenesis is also involved in many abnormal pathological processes such as tumor growth, tumor metastasis, and ocular vascular diseases such as diabetic retinopathy.

Angiogenesis involves a number of interdependent processes, including (a) activation of vascular endothelial cells, (b) decomposition of cell matrix proteins by endothelial cells expressing protease activity, (c) migration of endothelial cells to a potential growth sites, (d) proliferation of endothelial cells and (e) tube formation by differentiation of endothelial cells. Each of these processes is affected by a variety of promoter substances such as fibroblast growth factor (FGF), platelet-derived growth factor (PDGF), and vascular endothelial growth factors (VEGF). The vascular endothelial growth factors (collectively VEGF) play a crucial role in endothelial cell growth and differentiation. VEGF acts by binding to receptor protein-tyrosine kinases present in the endothelial cell membranes, which in turn initiate a cascade of signal transduction reactions that stimulate cell growth.

Inhibition of pathological angiogenesis has been proposed as a treatment for tumors. See, for example, Folkman et al. *Science*, 221, 719, (1983). The basic concept of such treatment is that, since tumors require vascularization to grow, inhibition of blood vessel formation, through the administration of angiogenesis inhibiting compounds, will prevent tumor growth by starving the tumor of its blood supply. A disadvantage of his approach is that angiogenesis inhibitors must be administered on a relatively continuous basis to prevent tumor growth. A cessation in delivery of the inhibitor can lead to a resumption of tumor growth. A DNA composition effective for eliciting an antiangiogenic immune response would be an attractive preventative agent against tumor formation.

There is a continuing need for a generally effective compositions for inhibiting angiogenesis and growth of a variety of tumors without the need for targeting specific tumor antigens. The present invention satisfies this need.

SUMMARY OF THE INVENTION

A DNA composition effective for inhibiting endothelial cell proliferation comprises a DNA construct that encodes a VEGF receptor polypeptide, which can be a full length VEGF receptor or an immunogenic fragment of a VEGF receptor, which is capable of eliciting an immune response against vascular endothelial cells, is expressible in immune cells, and is incorporated in a pharmaceutically acceptable carrier. VEGF receptors include VEGFR-2 (KDR; SEQ ID NO: 2), VEGFR-1 (Flt-1; SEQ ID NO: 4), and Flk-1 (SEQ ID NO: 6; the murine homolog of KDR), e.g., DNA sequences set forth in SEQ ID NO: 1, SEQ ID NO: 3, and SEQ ID NO 5, respectively. Preferably, immunogenic fragments of a VEGF receptor consist of about 8 to about 10 consecutive amino acid residues of a VEGF receptor.

The DNA compositions of the invention can encode a single immunogenic fragment of the VEGF receptor, a plurality of immunogenic fragments of the VEGF receptor in the form of a "minigene.", or an entire VEGF receptor. When the compositions encode two or more immunogenic fragments of a VEGF receptor, one fragment preferably is linked to another fragment in a linear manner, i.e., by a spacer peptide.

The DNA composition can comprise a linear nucleic acid such as a purified DNA construct, or a DNA construct incorporated in a plasmid vector. Preferably, the DNA construct is incorporated in an attenuated bacterial or viral vector in a manner such that the polypeptide encoded by the construct will be expressed in immune cells (e.g., macrophages and/or dendritic cells) within the subject to which the DNA composition has been administered. In this manner, the DNA compositions of the present invention stimulate formation of cytotoxic T lymphocytes (CTLs) active against proliferating endothelial cells that overexpress a VEGF receptor.

Endothelial cells form the lining of mammalian vascular tissue. The proliferation of endothelial cells is a key process in angiogenesis. The compositions of the present invention provide a method for producing long term inhibition of angiogenesis in an organism treated with the composition by eliciting an immune response against proliferating endothelial cells. Non-proliferating endothelial cells, such as the linings of established blood vessels, do not present significant quantities of VEGF receptor antigens, and thus remain substantially unaffected by the CTLs that are produced in response to the DNA compositions.

In a method aspect of the present invention, a DNA composition is utilized to provide long term inhibition of endothelial cell proliferation in a treated patient. In one method embodiment, a DNA composition (vaccine) comprising a polynucleotide construct encoding a VEGF receptor polypeptide is administered orally to a patient in need of inhibition of endothelial cell proliferation in an amount that is sufficient to elicit an immune response against proliferating endothelial cells.

The present invention also provides a method of inhibiting angiogenesis in a patient treated with a DNA composition of the invention. In such a method embodiment, an immune response eliciting amount of a DNA composition that includes a DNA construct encoding a VEGF receptor polypeptide is administered to a patient suffering from an angiogenesis-related disease.

In yet another method aspect of the present invention, tumor growth is inhibited by treating a patient with a DNA composition of the invention. In such a method embodiment, an immune response-eliciting amount of a DNA composition comprising a DNA construct operably encoding a VEGF receptor polypeptide is administered to a patient having a growing tumor. Administration of the composition results in tumor growth arrest. Destruction of proliferating endothelial cells by the patient's immune system prevents vascularization of the tumor, in essence starving the tumor to death.

In the method embodiments of the present invention, the DNA compositions can be administered enterally, such as by oral administration, or perenterally, such as by injection or intravenous infusion. The VEGF receptor polypeptide can be a full length VEGF receptor or an immunogenic fragment thereof.

The compositions of the present invention are useful for treatment and prevention of a number of disease states. For example, a patient suffering from a cancer, diabetic retinopathy, and the like, can benefit from immunization by the compositions of the present invention.

BRIEF DESCRIPTION OF THE DRAWINGS

In the Drawings, FIG. 1 depicts the DNA sequence encoding human KDR, SEQ ID NO: 1.

FIG. 2 depicts the protein sequence of human KDR, SEQ ID NO: 2.

FIG. 3 depicts the DNA sequence encoding human Flt-1, SEQ ID NO: 3.

FIG. 4 depicts the protein sequence of human Flt-1, SEQ ID NO: 4.

FIG. 5 depicts the DNA sequence encoding mouse Flk-1, SEQ ID NO: 5.

FIG. 6 depicts the protein sequence of human Flk-1, SEQ ID NO: 6.

FIG. 16. (A) Masson's trichrome staining of CT-26 lung metastasis tumor sections prepared 19 days after tumor cell challenge. The blue arrows indicate the blood vessels in the tumor. (B) Matrigel assay. Matrigel was implanted into mice vaccinated with either empty vector or pKd vaccines. Quantification of vessel growth by fluorimetry after staining of endothelium with FITC-labeled isolectin B4. The average fluorescence of Matrigel plugs from each group of mice is depicted by the bar graph (n=4; mean+SD). *, $P<0.05$ compared to empty vector control group.

DETAILED DESCRIPTION OF PREFERRED EMBODIMENTS

Figure 7:
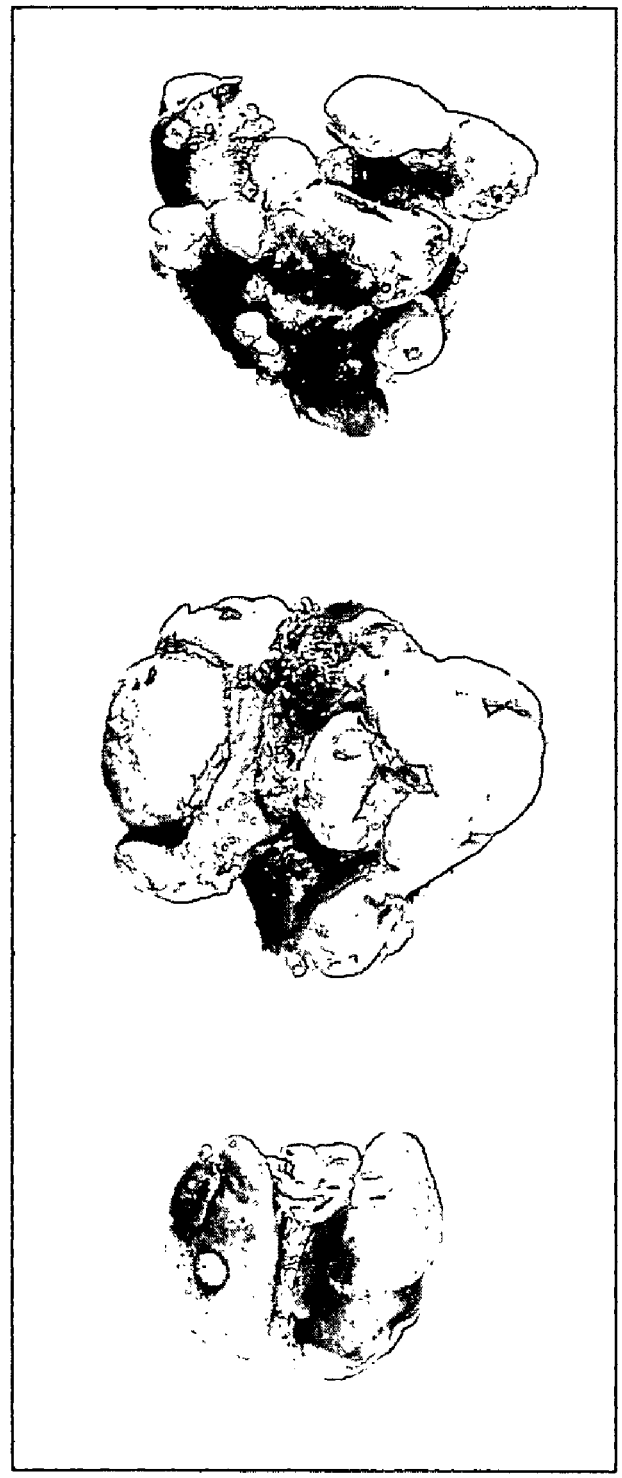
FIG. 7 is a pictorial representation of mouse lungs having varying levels of tumor coverage ranging from >50% coverage (labeled 3) to <10% coverage (labeled 1).

A DNA composition effective for inhibiting endothelial cell proliferation comprises a DNA construct that encodes a vascular endothelial growth factor (VEGF) receptor or at least one immunogenic fragment thereof capable of eliciting an immune response against vascular endothelial cells, incorporated in a pharmaceutically acceptable carrier. The VEGF receptor or immunogenic fragment thereof is expressible in immune cells. The term "DNA construct" as used herein and in the appended claims means a synthetic DNA structure that can be transcribed in target cells. The construct can comprise a linear nucleic acid, such as a purified DNA, or preferably, DNA incorporated in a plasmid vector. The DNA can also be incorporated in a viral or bacterial vector, preferably an attenuated viral or bacterial vector that is non-pathogenic. The DNA construct is capable of being expressed in immune cells (e.g., macrophages and/or dendritic cells) in a subject to which the DNA composition has been administered. As used herein and in the appended claims, the term "VEGF receptor polypeptide" includes full length VEGF receptors, as well as immunogenic fragments thereof, as described herein.

Suitable DNA constructs are those that encode a VEGF receptor such as VEGFR-2 (KDR; SEQ ID NO: 2), VEGFR-1 (Flt-1; SEQ ID NO: 4), and Flk-1 (SEQ ID NO: 6), e.g., DNA sequences SEQ ID NO: 1, SEQ ID NO: 3, and SEQ ID NO 5, respectively, or an immunogenic fragment (i.e., an epitope) thereof. Preferably, the DNA construct encodes two or more immunogenic VEGF receptor fragments linked together in linear fashion by a linker peptide between each fragment.

Five VEGF sub-types have been identified, including VEGF-1 (also known as VEGF-A), VEGF-2 (also known as VEGF-C), VEGF-B, VEGF-D and VEGF-E. See, for example, U.S. Pat. No. 6,235,713 to Achen et al. and references cited therein. VEGF receptors are protein-tyrosine kinases specific to endothelial cells. Several receptor protein-tyrosine kinases that are specific to endothelial cells have been identified, including Flt-1 (VEGF receptor 1; VEGFR-1), KDR (VEGFR-2), Flk-1 (the murine homolog of KDR), Flt-4 (VEGFR-3), Tie, Tie-2 and Tek, several of which are VEGF receptors.

Preferably, the compositions of the present invention comprise a DNA construct that encodes one or more VEGF receptor protein, such as a tyrosine kinase that is specific to endothelial cells, including, for example Flt-1, KDR, Flk-1, functional homologs thereof, or at least one immunogenic fragment (epitope) thereof. The functional homologs preferably share at least about 80% homology with the aforementioned VEGF receptor proteins. Immunogenic fragments of VEGF receptors preferably consist of about 8 to 10 contiguous amino acid resides from a VEGF receptor, i.e., from an epitope region of the protein.

In some preferred embodiments, the DNA construct encodes two or more (e.g., 2 to 5) immunogenic fragments of a VEGF receptor. The DNA construct preferably encodes the fragments linked together by a spacer peptide (e.g., AAA or AAY) between each fragment. Preferably, the DNA construct encoding an immunogenic fragment of a VEGF receptor also encodes a membrane-translocating peptide, such as the HIVtat peptide, connected to the N-terminus of the immunogenic fragment of legumain by a spacer peptide. When the DNA construct encodes two or more immunogenic fragments, the membrane-translocating peptide preferably is linked to the first fragment from the N-terminus thereof.

Immunogenic fragments of VEGF receptors can be identified by the HLA Binding Predictions program provided by the Bioinformatics & Molecular Analysis Section (BIMAS) of the National Institutes of Health (NIH) at the NIH www website, which is incorporated herein by reference.

The DNA compositions of the present invention stimulate formation of CTLs that are active against proliferating endothelial cells that overexpress a VEGF receptor. Because VEGF receptors are only substantially expressed on proliferating endothelial cells, a CTL that forms in response to contact with a composition of the invention will substantially target only tissues where active angiogenesis (e.g., vascularization) is occurring. Non-proliferating endothelial cells, such as the linings of established blood vessels, are substantially lacking in VEGF receptor antigens and are thus not affected by a CTL elicited by the DNA composition of the invention.

In a preferred embodiment, the DNA composition comprises a polynucleotide sequence that operably encodes at least one immunogenic fragment of a VEGF receptor incorporated in a vector capable of expressing the immunogenic fragment in an immune cell after being taken up by the immune cell. This composition can promote activation of naive T cells, both directly and indirectly, through the intervention of dendritic cells.

In some preferred embodiments, the DNA composition further comprises a DNA construct encoding an immune effector protein expressible in immune cells. As used herein and in the appended claims the phrase "immune effector protein" means a protein that is involved in regulation of an immune system pathway. Preferably, the immune effector protein is a cytokine.

Cytokines are proteins and polypeptides produced by cells that can affect the behavior of other cells, such as cell proliferation, cell differentiation, regulation of immune responses, hematopoiesis, and inflammatory responses. Cytokines have been classified into a number of families, including chemokines, hematopoietins, immunoglobulins, tumor necrosis factors, and a variety of unassigned molecules. See generally *Oxford Dictionary of Biochemistry and Molecular Biology*, Revised Edition, Oxford University Press, 2000; and C. A. Janeway, P. Travers, M. Walport and M. Schlomchik, *Immunobiology*, Fifth Edition, Garland Publishing, 2001 (hereinafter "Janeway and Travers"). A concise classification of cytokines is presented in Janeway and Travers, Appendix III, pages 677-679, the relevant disclosures of which are incorporated herein by reference.

Hematopoietins include, for example erythropoietin, interleukin-2 (IL-2, a 133 amino acid protein produced by T cells and involved in T cell proliferation), IL-3, IL-4, IL-5, IL-6, IL-7, IL-9, IL-11, IL-13, IL-15 (a 114 amino acid IL-2-like protein, which stimulates the growth of intestinal epithelium, T cells, and NK cells), granulocyte colony-stimulating factor (G-CSF), granulocyte-macrophage colony-stimulating factor (GM-CSF), oncostatin M (OSM), and leukemia inhibitory factor (LIF).

Interferons include, for example, IFN-α, IFN-β, and IFN-γ (a 143 amino acid homodimeric protein produced by T cells and NK cells, which is involved in macrophage activation, increased expression of MHC molecules and antigen processing components, IG class switching, and suppression of $T_H2$).

Immunoglobulins include, for example, B7.1 (CD80), and B7.2 (CD86), both of which co-stimulate T cell responses.

The tumor necrosis factor (TNF) family includes, for example, TNF-α, TNF-β (lymphotoxin), lymphotoxin-β(LT-β), CD40 ligands, Fas ligand, CD27 ligand, CD30 ligand, 4-1BB ligand, Trail, and OPG ligand.

The biological roles of CD40 ligand (CD40L), particularly its interaction with CD40 expressed on antigen presenting cells during costimulation of T cell activation, are well known in the art. CD40 is a 48 kDa glycoprotein expressed on the surface of all mature B cells, most mature B-cell malignancies, and some early B-cell acute lymphocytic leukemias, but it is not expressed on plasma cells, Clark, *Tissue Antigens* 1990, 35:33-36. CD40L, a type II membrane protein of about 35 kDa, is expressed on the surface of T cells upon antigen recognition. Members of the TNF family are biologically most active when expressed as homotrimers. CD40L is no exception in this regard and can be expressed as a homotrimer (CD40LT) by modification of a 33 amino acid leucine zipper motif fused to the N-terminus of the entire extracellular domain of this ligand. CD40LT DNA has been reported by Gurunathan et al. *J. Immunol.* 1998, 161:4563, to enhance cellular immune responses such as induction of IFN-γ and cytolytic T cell activity when mice were vaccinated with DNA encoding the highly immunogenic model antigen β-galactosidase.

CD40LT is an important factor in the activation of T cells necessary to induce an effective protective immunity against tumor self-antigens. Once MHC class I antigen:peptide complexes are taken up by dendritic cells (DCs) and presented to naive T cells, the first antigen signal is delivered via T cell receptors (TCR), followed by upregulation of CD40LT. On the T cell surface, CD40LT then induces costimulatory activity on DCs via CD40-CD40LT interactions. Thus primed, these APCs can express costimulatory molecules B7.1

(CD80) and B7.2 (CD86), which sends a second costimulatory signal to T cells via interaction with CD28, an event required for full activation of T cells to concurrently produce pro-inflammatory cytokines INF-γ and IL12, and to perform effector functions.

Various cytokines that are not assigned to a particular family include, for example, tumor growth factor-β, (TGF-β), IL-1α, IL-1β, IL-1 RA, IL-10, IL-12 (natural killer cell stimulatory factor; a heterodimer having a 197 amino acid chain and a 306 amino acid chain, which is involved in NK cell activation and induction of T cell differentiation to $T_H1$-like cells), macrophage inhibitory factor (MIF), IL-16, IL-17 (a cytokine production-inducing factor, which induces cytokine production in epithelia, endothelia, and fibroblasts), and IL-18.

Chemokines are a family of cytokines that are relatively small chemoattractant proteins and polypeptides, which stimulate the migration and activation of various cells, such as leucocyte migration (e.g., phagocytes and lymphocytes). Chemokines play a role in inflammation and other immune responses. Chemokines have been classified into a number of families, including the C chemokines, CC chemokines, CXC chemokines, and $CX_3C$ chemokines. The names refer to the number and spacing of cysteine (c) residues in the molecules; C chemokines having one cysteine, CC chemokines having two contiguous cysteines, CXC having two cysteines separated by a single amino acid residue, and $CX_3C$ chemokines having two cysteines separated by three amino acid residues. Chemokines interact with a number of chemokine receptors present on cell surfaces. See Janeway and Travers, Appendix IV, page 680, which is incorporated herein by reference.

In addition, chemokines can have immunomodulating activity and have been implicated in immune responses to cancer. For example, murine 6Ckine/SLC, the mouse analog of the human secondary lymphoid tissue chemokine (SLC), now commonly referred to as CCL21, has been reported to induce an antitumor response in a C-26 colon carcinoma tumor cell line. See Vicari, et al. *J. Immunol.* 2000; 165(4): 1992-2000. Human CCL21 and its murine counterpart, 6Ckine/SLC, are classified as CC chemokines, which interact with the CCR7 chemokine receptor. Murine 6Ckine/SLC (muCCL21) is also reported by Vicari et al. to be a ligand for the CXCR3 chemokine receptor. Human CCL21, murine muCCL21 and a variety of other chemokines are implicated in the regulation of various immune system cells such as dendritic cells, T cells, and natural killer (NK) cells.

Mig and IP-10 are CXC chemokines that interact with the CXCR3 receptor, which is associated with activated T cells. Lymphotactin is a C chemokine, which interacts with the XCR1 receptor associated with T cells and NK cells. Fractalkine is a $CX_3C$ chemokine, which interact with the $CX_3CR1$ receptor that is associated with T cells, monocytes and neutrophils.

Particularly preferred immune effector proteins to be encoded by the DNA compositions of the present invention include cytokines IL-2 (a hematopoietin), CCL21 (a chemokine), as well as CD40 ligands such as CD40 ligand trimer (CD40LT), a TNF family cytokine.

DNA and protein sequences for human IL-2 have been published in GenBank, Accession No. BC070338, the disclosures of which are incorporated herein by reference. The DNA and protein sequences of murine IL-2 have been in GenBank, Accession No. NM 008366, the disclosures of which are incorporated herein by reference.

DNA and protein sequences for human CCL21 have been published in GenBank, Accession No. AB002409, the disclosures of which are incorporated herein by reference.

Human CD40 ligand (CD40L) is a 261 amino acid protein, which exists as a trimer (CD40LT) in its most active form. The DNA sequence encoding human CD40L (also known as CD154) has been published in GenBank, Accession No. NM 000074, the disclosure of which is incorporated herein by reference.

A DNA composition of the invention can be utilized to provide long term inhibition of tumor growth and/or tumor metastases in a patient treated with the composition. In a preferred embodiment, the DNA composition is administered in conjunction with an antitumor chemotherapeutic agent. The DNA composition can be administered together with the chemotherapeutic agent in a combined dosage form, or the composition and chemotherapeutic agent can be administered in separate dosage forms and at separate dosage intervals tailored to the pharmacology of the chemotherapeutic agent being administered.

Chemotherapeutic agents useful in combination with the DNA compositions of the present invention include antitumor agents such as doxorubicin, paclitaxol, a cyclophosphamide, etoposide, 5-fluorouracil, methotrexate, and the like.

As used herein, the term "immunity" refers to long term immunological protection against the virulent form of the infectious agent or tumor antigen. The term "immunization" refers to prophylactic exposure to an antigen of a pathogenic agent derived from a non-virulent source, which results in immunity to the pathogen in the treated subject.

A DNA composition of the present invention preferably comprises a nucleotide sequence that encodes a VEGF receptor or at least an immunogenic fragment of a VEGF receptor protein, operably linked to regulatory elements needed for gene expression in immune cells of the subject to be treated.

Useful DNA constructs preferably include regulatory elements necessary for expression of nucleotides. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired polypeptide. Regulatory elements are preferably selected that are operable in immune cells of the subject to which they are to be administered.

Initiation codons and stop codons are preferably included as part of a nucleotide sequence that encodes the immunogenic fragment of the VEGF receptor protein in a DNA composition of the present invention. The initiation and termination codons must be in frame with the coding sequence.

Promoters and polyadenylation signals included in a composition of the present invention are preferably selected to be functional within the cells of the subject to be treated.

Examples of promoters useful in the compositions of the present invention, especially in the production of a composition for use in humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein.

Examples of polyadenylation signals useful in the compositions of the present invention, especially in the production of a composition for humans, include but are not limited to SV40 polyadenylation signals and LTR polyadenylation signals.

In addition to the regulatory elements required for DNA expression, other elements can also be included in the DNA molecule. Such additional elements include enhancers. The enhancer can be, for example, human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. One having ordinary skill in the art can produce DNA constructs that are functional in a given subject species.

The DNA constructs of the present compositions can be "naked" DNA as defined in Restifo et al. *Gene Therapy* 7, 89-92 (2000), the pertinent disclosure of which is incorporated by reference. Alternatively, the DNA can be operably incorporated in a vector. Useful delivery vectors include biodegradable microcapsules, immuno-stimulating complexes (ISCOMs) or liposomes, and genetically engineered attenuated live vectors such as viruses or bacteria.

Examples of suitable attenuated live bacterial vectors include *Salmonella typhimurium, Salmonella typhi, Shigella, Bacillus, Lactobacillus, Bacille Calmette-Guerin* (BCG), *Escherichia coli, Vibrio cholerae, Campylobacter,* or any other suitable bacterial vector, as is known in the art. Methods of transforming live bacterial vectors with an exogenous DNA construct are well described in the art. See, for example, Joseph Sambrook and David W. Russell, *Molecular Cloning, A Laboratory Manual,* 3rd Ed., Cold Spring Harbor Laboratory Press, Cold Spring Harbor, N.Y. (2001).

A preferred attenuated bacterial vector is an attenuated *Salmonella* carrier, which is the doubly attenuated strain of *S. typhimurium* designated as RE 88, and which includes the dam$^-$ and AroA$^-$ mutations, available from Remedyne Corporation (Goleta, Calif.). The attenuated *Salmonella* carrier is engineered to include DNA encoding a VEGF receptor polypeptide such as an immunogenic fragment of a VEGF receptor, which is expressible in immune cells of a mammal to which it is administered. The bacteria do not themselves express the immunogenic polypeptide, but rather deliver DNA encoding the polypeptide to immune cells, such as macrophages and dendritic cells (DCs), which in turn express the polypeptide. Such compositions can provide prolonged antitumor effects in murine models. Furthermore, in vivo depletion experiments of T cells indicated the involvement of CD8$^+$ but not CD4$^+$ T cells. The cytotoxic effect mediated by CD8$^+$ T cells in vitro is specifically directed against target proliferating endothelial cells that overexpress the VEGF receptors.

Preferred viral vectors include Bacteriophages, Herpes virus, Adenovirus, Polio virus, Vaccinia virus, and Avipox. Methods of transforming viral vector with an exogenous DNA construct are also well described in the art. See Sambrook and Russell, above.

Liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., *Biochemistry* 27:3917-3925 (1988); and H. Eibl, et al., *Biophysical Chemistry* 10:261-271 (1979). Alternatively, a microsphere such as a polylactide-coglycolide biodegradable microsphere can be utilized. A nucleic acid construct is encapsulated or otherwise complexed with the liposome or microsphere for delivery of the nucleic acid to a tissue, as is known in the art.

The method aspects of the present invention comprise the step of administering DNA compositions of the invention to a mammal, such as a human. In some preferred embodiments, the DNA polynucleotides are administered orally, intramuscularly, intranasally, intraperitoneally, subcutaneously, intradermally, or topically.

In a method aspect of the present invention, a DNA composition of the invention can be utilized as a vaccine to provide long term inhibition of endothelial cell proliferation in a patient treated with the vaccine. In one preferred method embodiment, a DNA composition comprising a polynucleotide construct operably encoding a VEGF receptor polypeptide is administered to a mammal in need of inhibition of endothelial cell proliferation, in an amount that is sufficient to elicit an immune response against proliferating endothelial cells. The terms "DNA composition" and "DNA vaccine" are used interchangeably herein for convenience, with respect to the methods of the present invention.

The present invention also provides a method of inhibiting angiogenesis in a mammal treated with the DNA vaccine. In such a method embodiment, a vaccine comprising a DNA construct operably encoding a VEGF receptor polypeptide is administered to a mammal suffering from an angiogenesis related disease, in an amount sufficient to elicit an immune response against proliferating endothelial cells.

In yet another method aspect of the present invention, tumor growth is inhibited by treatment of a mammal with a DNA vaccine. In such a method embodiment, an immune response eliciting amount of a vaccine comprising a DNA construct operably encoding a VEGF receptor polypeptide is administered to a mammal having a growing tumor. Treatment with the vaccine results in tumor growth arrest by immunizing the mammal against proliferating endothelial cells. Destruction of proliferating endothelial cells by the mammal's immune system prevents, or at least minimizes vascularization of the tumor.

In the method embodiments of the present invention, the vaccines can be administered enterally, such as by oral administration, or by intramuscular injection. Preferably, the mammal treated with the inventive vaccine is a human. A patient suffering from cancer, such as lung or colon carcinoma, or prostate tumors, diabetic retinopathy, and the like, can benefit from immunization by the vaccines of the present invention.

Compositions of the present invention preferably are formulated with pharmaceutically acceptable carriers or excipients such as water, saline, dextrose, glycerol, and the like, and combinations thereof. The compositions can also contain auxiliary substances such as wetting agents, emulsifying agents, buffers, and the like.

The compositions of the present invention are preferably administered orally to a mammal, such as a human, as a solution or suspension in a pharmaceutically acceptable carrier, at a DNA concentration in the range of about 1 to about 10 micrograms per milliliter. The appropriate dosage will depend upon the subject to be vaccinated, and in part upon the judgment of the medical practitioner administering or requesting administration of the vaccine.

The compositions of the present invention can be packaged in suitably sterilized containers such as ampules, bottles, or vials, either in multi-dose or in unit dosage forms. The containers are preferably hermetically sealed after being filled with a compositions of the invention. Preferably, the compositions are packaged in a container having a label affixed thereto, which label identifies the compositions, and bears a notice in a form prescribed by a government agency such as the United States Food and Drug Administration reflecting approval of the vaccine under appropriate laws, dosage information, and the like. The label preferably contains information about the composition that is useful to an health care professional administering the compositions to a patient. The package also preferably contains printed informational materials relating to the administration of the composition, instructions, indications, and any necessary required warnings.

The amino acid sequences of VEGF receptor proteins have been disclosed in the art, as have the nucleic acid sequences encoding these proteins. The nucleic acid sequence encoding KDR (FIG. 1, SEQ ID NO: 1), and its corresponding protein sequence (FIG. 2, SEQ ID NO: 2) have been published by Yu et al., in the EMBL database of the European Bioinformatics Institute, Wellcome Trust Genome Campus, Hinxton, Cambridge CB10 1 SD, UK (EMBL accession number is EMBL: AF063658), the disclosures of which are incorporated herein by reference. The nucleic acid sequence encoding Flt-1 (FIG. 3, SEQ ID NO: 3), and its corresponding protein sequence (FIG. 4, SEQ ID NO: 4) have been published by Yu et al., in the EMBL database of the European Bioinformatics Institute, Wellcome Trust Genome Campus, Hinxton, Cambridge CB10 1SD, UK (EMBL accession number is EMBL: AF063657), the disclosures of which are incorporated herein by reference.

The nucleic acid sequence encoding Flk-1, and its corresponding protein sequence have been published by Mathews et al., *Proc. Natl. Acad. Sci. USA* 1991, 88:9026-9030, and the structures were corrected by Quinn et al., *Proc. Natl. Acad. Sci. USA* 1991, 90:7533-7537, the relevant disclosures of which are incorporated herein by reference. The corrected DNA sequence of Flk-1 is provided in FIG. 5 as SEQ ID NO: 5, and the corrected protein sequence of Flk-1 is provided in FIG. 6 as SEQ ID NO:6.

Due to the inherent degeneracy of the genetic code, other DNA sequences which encode substantially the same or a functionally equivalent amino acid sequence to VEGF receptor proteins such as KDR, Flk-1 and Flt-1, can be used in the practice of the invention. Such DNA sequences include those which are capable of hybridizing to the VEGF receptor sequences as well. Preferably the functionally equivalent homologs of the VEGF receptor protein DNA shares at least about 80% homology with the DNA encoding the aforementioned VEGF receptor proteins.

Altered DNA sequences which can be used in accordance with the invention include deletions, additions or substitutions of different nucleotide residues resulting in a sequence that encodes the same or a functionally equivalent gene product. The gene product itself may contain deletions, additions or substitutions of amino acid residues within the VEGF receptor sequences, which result in a silent change, thus producing a functionally equivalent VEGF receptor proteins. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. As used herein, a functionally equivalent VEGF receptor refers to a receptor that binds to VEGF or fragments thereof, but not necessarily with the same binding affinity of its counterpart native KDR, Flk-1 or Flt-1.

The DNA constructs may be engineered in order to alter the VEGF receptor coding sequence for a variety of ends including, but not limited to, alterations that modify processing and expression of the gene product. For example, mutations may be introduced using techniques that are well known in the art, e.g. site-directed mutagenesis, to insert new restriction sites, to alter glycosylation patterns, phosphorylation, etc.

Mouse Flk-1 (SEQ ID NO: 6) shares an approximately 85% homology with human KDR (SEQ ID NO: 2) and plays an analogous role in mouse physiology to the role of KDR in humans. In fact, VEGFR-2 is often referred to as KDR/Flk-1, reflecting the close analogy between these two VEGF receptor homologs. For this reason, treatment of mice with a DNA vaccine of the invention, encoding Flk-1 (e.g., DNA SEQ ID NO: 5) was chosen as a suitable model for human DNA vaccines encoding KDR.

The following examples are provided to further illustrate the features and embodiments of the present invention, and are not meant to be limiting.

Materials, Methods and Examples.

Materials. C57/BL/6J and Balb/C mice were obtained from the Scripps Research Institute breeding facility. The murine tumor cell lines used for evaluation included the melanoma cell line B16 and the colon carcinoma cell line CT26, all of which were obtained from Dr. I. J. Fidler, MD Anderson Cancer Center, Houston, Tex. The murine Lewis lung cancer cell line D121 was obtained from Dr. Lea Eisenbach, Weizmann Institute, Rehovot, Israel. The DNA encoding Flk-1 was kindly provided by Dr. Lemischka (Princeton University, Princeton, N.J.), and was cloned into the pcDNA3.1 eucaryotic expression vector provided by Invitrogen, Huntsville, Ala., using the restriction sites KpnI and XbaI. An attenuated strain of *Salmonella typhimurium* was provided by B.A.D. Stocker (Stanford University, Stanford, Calif.). Antibodies were obtained from BD Biosciences, Bedford, Mass. T-STIM culture supplement was obtained from BD Biosciences, Bedford, Mass. Fluorescein isothiocyanate (FITC) and R-Phycoerythrin (PE) were obtained from Molecular Probes, Eugene, Oreg. FITC-labeled and PE-labeled antibodies were prepared according to the manufacturer's recommended protocols.

EXAMPLE 1

Preparation of a DNA Vaccine Encoding Flk-1

The pcDNA3.1 vector containing Flk-1 DNA (SEQ ID NO: 5; about 10 pg to about 0.1 µg of pDNA) was electroporated into freshly prepared attenuated *Salmonella typhimurium*, utilizing a Bio-Rad Pulser at 2.5 kV, 25 µF, and 200 Ohm according to the manufacturer's recommended procedures. *Salmonella* containing the vector were selected on ampicillin-containing plates. Colonies were picked the next day and cultured overnight in LB broth (EM Science, Gibbstown, N.J.) with ampicillin added. The bacteria were isolated and washed in phosphate buffered saline (PBS). The washed bacteria were then suspended in PBS medium at a concentration of about $1\times10^9$ recombinant *Salmonella* per milliliter of PBS, to form a vaccine solution for later use. The vaccine was stored in sealed ampules until used. A "control vaccine" consisting of *Salmonella* transformed with the pcDNA3.1 vector alone (no Flk-1 DNA) was also prepared according to the same procedure. The plasmid DNA was stored at about −80° C. before transforming the Salmonella.

EXAMPLE 2

Vaccination of Mice with a DNA Vaccine Encoding Flk-1

Balb/C mice (about 6 mice per treatment group) were vaccinated with the DNA vaccine of Example 1 (about 1×10⁸ recombinant *Salmonella* in about 100 μl of PBS) by oral gavage, three times at two week intervals. Another group of mice were vaccinated with control vaccine (consisting of attenuated *Salmonella* containing the empty vector) according to the same schedule as the mice vaccinated with the inventive vaccine.

EXAMPLE 3

Evaluation of Tumor Resistance of Vaccinated Mice

About two weeks after the third vaccination, Balb/C mice from Example 2 (about 6 mice per treatment group) were challenged with either about 1×10⁵ B16 melanoma cells (subcutaneously), about 1×10⁵ D121 Lewis lung carcinoma cells (subcutaneously), or about 7.5×10⁴ CT26 colon carcinoma cells (intravenously). The subcutaneous Lewis lung tumors were surgically removed after about two weeks of growth to allow spontaneous dissemination to the lung. Subcutaneous tumor growth was measured in two dimensions every other day, and tumor volume was calculated according to the formula:

$$\text{volume} = (\text{width}^2)(\text{length} \div 2)$$

for each tumor. The amount of spontaneous metastasis of D121 to the lungs was evaluated about 30 days after removal of the subcutaneous primary tumor. The mice were sacrificed and necropsied, and the tumor burdens of the lungs were evaluated according to the percentage of the lung surface that was covered by tumor and scored as "0" for no tumor, "1" for less than about 20% tumor coverage, "2" for about 20 to about 30% tumor coverage, and "3" for greater than about 50% tumor coverage. FIG. 7 shows pictures of lungs from three mice challenged with D121 Lewis lung carcinoma cells. The lower lung was scored 1, whereas the upper two lungs were scored 3, having a large proportion of the lung surface covered by tumors. Animals that died prior to the 30 day evaluation were given a "+" score.

The results of these evaluations are provided in Tables 1-4, and in FIGS. 8-10, discussed in detail below.

TABLE 1

Tumor Metastasis in Balb/C Mice Challenged with D121 Lewis Lung Carcinoma Cells.

| Mouse Vaccination Group | Metastatic Scores |
| --- | --- |
| Control - vaccination with untransformed Salmonella | 3, 3, 3, 3, +, + |
| Control - vaccination with control vaccine (containing empty vector) | 3, 3, 3, 3, +, + |
| Vaccination with DNA Vaccine of Example 1 (containing Flk-1) | 0, 0, 1, 1, 1, 2, 2 |

The Balb/C mice that were challenged by intravenous injection of CT-26 colon carcinoma cells were evaluated for mortality over about a 63 day (7 week) period. Mortality information is presented in Table 2 below, and graphically illustrated in FIG. 8.

Figure 8:
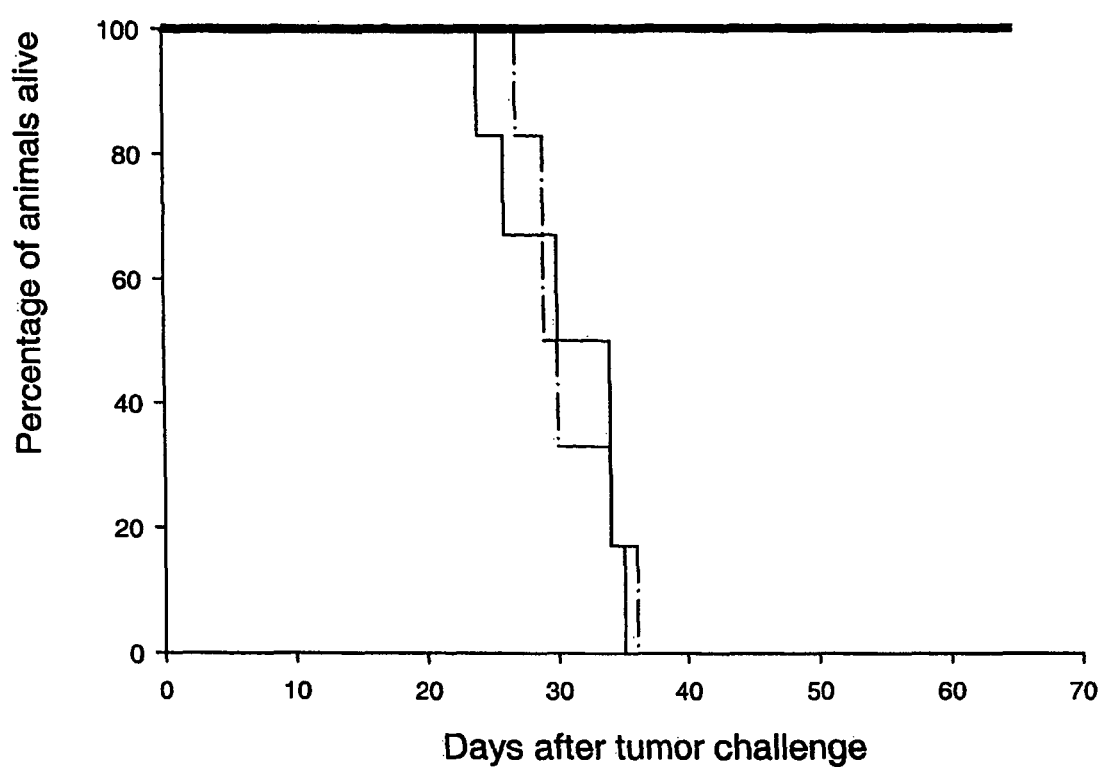
FIG. 8 is a graphical representation of data demonstrating that mice treated with a DNA composition encoding a VEGFR polypeptide (solid, heavy black line) and challenged by intravenous injection of CT-26 colon carcinoma cells, exhibited significantly reduced mortality relative to two control groups of mice (naive mice: solid thin line; control: dash-dot line).

In FIG. 8, the % survival of mice treated with the inventive vaccine of Example 1 is indicated by the heavy, solid line at 100% survival. The % survival of naive mice (no vaccination) challenged with the C26 cell is indicated by the solid, thin line, whereas, the % survival of the mice treated with the control vaccine (no Flk-1 DNA) is indicated by the dot-dash line.

TABLE 2

Suppression of Mortality in Balb/C Mice Immunized With the Vaccine of Example 1 and Challenged with CT 26 Carcinoma.

| Treatment | % Survival on Day 30 | % Survival on Day 36 | % Survival on Day 63 |
| --- | --- | --- | --- |
| Control, No Vaccine | 50 | 0 | 0 |
| Control Vaccine | 33 | 0 | 0 |
| Vaccine of Ex. 1 | 100 | 100 | 100 |

The suppression of growth of the primary (subcutaneous) tumor in D121 challenged Balb/C mice was evaluated by determination of primary tumor volume at day 14 after challenge. Results are presented in Table 3 below, and graphically illustrated in FIG. 9.

Figure 9:
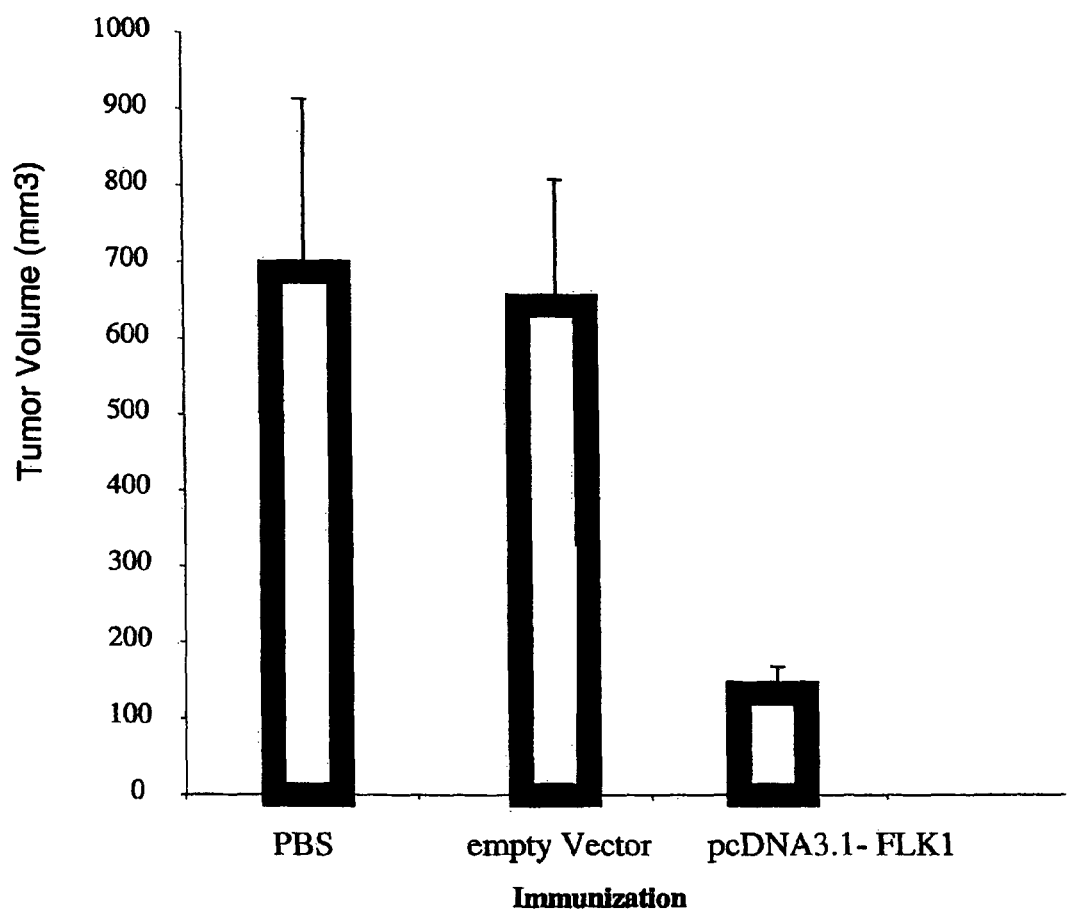
FIG. 9 is a graphical representation of data demonstrating the suppression of D121 Lewis lung carcinoma tumor growth in mice treated with a DNA composition encoding a VEGFR polypeptide (pcDNA3.1-FLK-1) relative to two control groups of mice.

In FIG. 9, the first bar, labeled "PBS" indicates mice that were not vaccinated (naive mice), the middle bar, labeled "empty vector" indicates mice treated with the control vaccine, and the third bar, labeled "pcDNA3.1-Flk1" indicates mice immunized with the inventive vaccine of Example 1.

TABLE 3

Suppression of Subcutaneous D121 Carcinoma Tumor in Balb/C Mice Immunized With the Vaccine of Example 1.

| Treatment | Tumor volume mm³ | Standard Deviation |
| --- | --- | --- |
| Control No Vaccine | 665 | 227 |
| Control Vaccine | 641 | 157 |
| Vaccine of Ex. 1 | 183 | 35 |

Suppression of subcutaneous B16 melanoma tumor growth was evaluated by monitoring the subcutaneous tumor volume over a period of about 17 days after tumor challenge. Results are presented in Table 4 and graphically illustrated in FIG. 10 below. In FIG. 10, average tumor volume data indicated by (●) represents mice immunized with the inventive vaccine of Example 1, whereas data indicated by (○) indicates mice treated with the control vaccine.

TABLE 4

Suppression of Subcutaneous B16 Melanoma Tumor in Balb/C Mice Immunized With the Vaccine of Example 1.

| Treatment | Tumor Volume (mm³) on Day | | | |
| --- | --- | --- | --- | --- |
| | 0 | 9 | 14 | 17 |
| Control Vaccine | 0 | 907 | 1273 | 4213 |
| Vaccine of Ex. 1 | 0 | 447 | 462 | 1063 |
| % Tumor Suppression | — | 51% | 64% | 75% |

EXAMPLE 4

Upregulation of CD25, CD69 and CD2 Activation Markers in Splenocytes (CD8+ T Cells) from Vaccinated Mice C5/7BL/6J mice (about 4 mice per treatment group) were vaccinated with the DNA vaccine of Example 1 and the control vaccine (no Flk-1) as described in Example 2. Splenocytes were isolated from the immunized mice and the control mouse group about six weeks after the third vaccination. The splenocyte cells were cultured for 24 hours together with cells from a B16 melanoma cell line transduced to express Flk-1 and with untransformed B16 cells in T cell medium (about 5 mL per culture) containing about 4% by volume of T-STIM culture supplement (Cat. #354115, BD Biosciences, Bedford, Mass.). The cells were then stained with FITC-conjugated CD8+ antibody and PE-conjugated antibodies of CD25, CD69, and CD2. The cell suspensions were evaluated using a Becton Dickenson FAC scan to determine the percentage of CD8+ T cells positive for CD25 and CD69 for each splenocyte/B16 melanoma cell combination. The results are presented in Table 5 and are illustrated graphically in FIG. 11.

TABLE 5

Upregulation of CD25, CD69 and CD2 Activation Markers in Splenocytes From Vaccinated Mice

| Treatment | % CD25 positive | % CD69 positive | CD2 positive mean fluorescence |
|---|---|---|---|
| Control vaccine + B16-Flk-1 cells | 9 | 18 | 570 mfu |
| DNA vaccine + B16 cells | 12 | 29 | 550 mfu |
| DNA vaccine + B16-Flk-1 cells | 21 | 35 | 700 mfu | mfu = mean fluorescence units.

The results provided in Tables 1-5 and FIGS. 8-11 demonstrate that the DNA vaccine of Example 1, comprising a DNA encoding Flk-1, the murine analog of KDR, can effectively immunize mice against a variety of tumor forming cancer cells. Although not intending to be bound by theory, it is believed that the vaccine acts by inhibiting angiogenesis in the tumor, i.e, preventing new blood vessel formation and effectively starving the tumor.

The data in Table 1 demonstrate that the inventive vaccine of Example 1 leads to a suppression of tumor metastasis to the lungs of mice challenged with D121 Lewis lung carcinoma. None of the mice immunized with the vaccine of Example 1 died, and all had less than about 50% tumor coverage on the lungs (2 had <20%). In contrast, two mice died from each control group and all of the remaining mice had greater than about 50% tumor coverage on the lungs.

The inventive vaccine of Example 1 also significantly decreased mortality of Balb-C mice that were challenged intravenously by CT-26 colon carcinoma cells, as demonstrated by the data in Table 2 and FIG. 8. All of the mice immunized with the vaccine of Example 1 survived the entire 63 day observation period after challenge. In the control groups, however, all of the mice had died by day 36 post challenge.

As demonstrated by the data in Table 3 and FIG. 9, subcutaneous D121 Lewis lung carcinoma tumor growth was suppressed by immunization with the inventive vaccine of Example 1 by a factor of about 4.3 to about 4.5, relative to the control mouse groups treated with no vaccine or the control vaccine.

Figure 10:
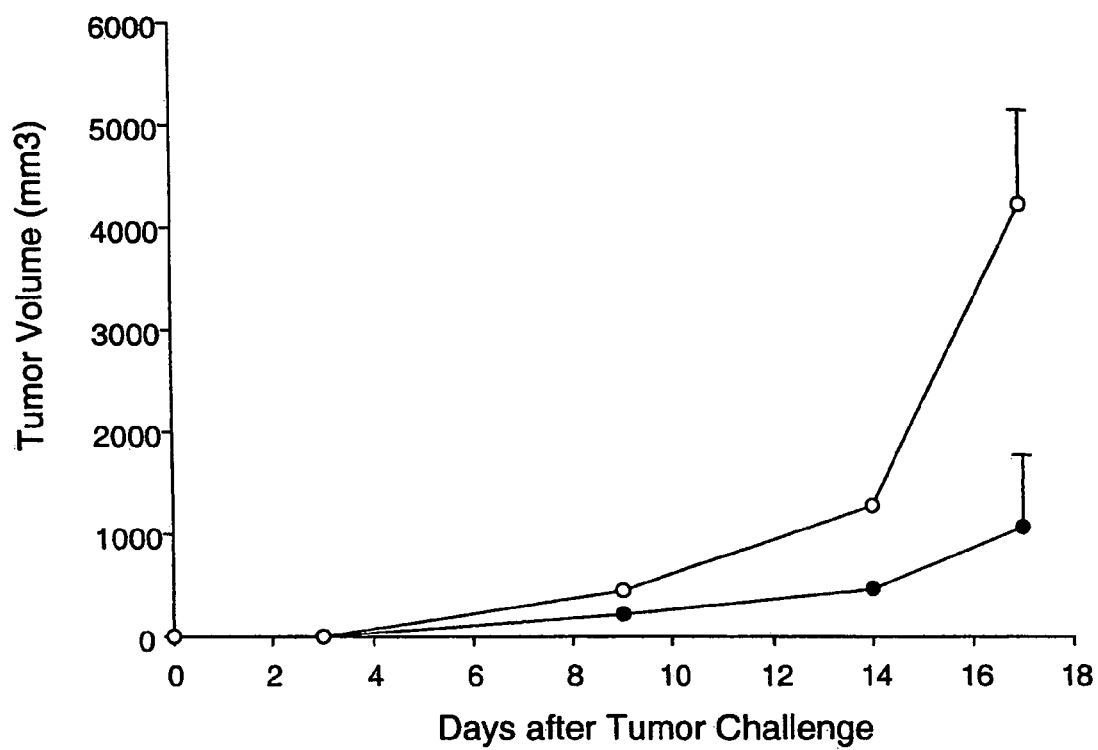
FIG. 10 is a graphical representation of data demonstrating the suppression of B16 melanoma tumor growth in mice vaccinated with a DNA composition encoding a VEGFR protein (●) relative to a control group (○).

Similarly, as shown in Table 4 and FIG. 10, subcutaneous B16 melanoma tumor growth was suppressed by a factor of about 4 in mice immunized with the inventive vaccine of Example 1, relative to tumor growth in the control group.

Figure 11:
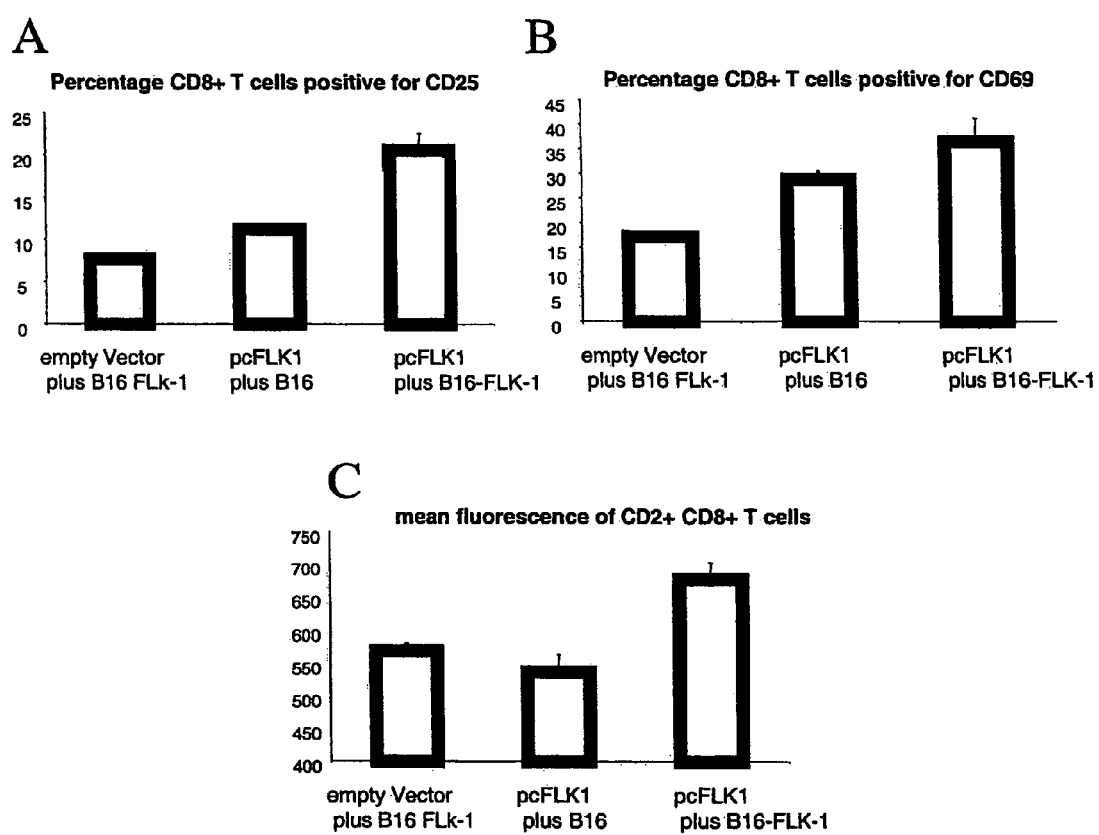
FIG. 11 is a graphical representation of data demonstrating the upregulation of CD25, CD69, and CD2 positive CD8+ T cells in mice treated with a DNA composition encoding a VEGFR polypeptide relative to a control group of mice.

The data in Table 5 and FIG. 11 show that splenocytes isolated from C57/BL/6J mice vaccinated with the DNA vaccine of Example 1 exhibited an upregulation of CD2, CD25 and CD69 activation markers relative to the control group of mice, when cultured with B16 melanoma cells transformed to present Flk-1 antigen.

The following additional non-limiting Examples further illustrate the compositions and methods of the present invention in which the VEGF receptor polypeptide is an immunogenic fragment of a VEGF receptor.

EXAMPLE 5

DNA Composition Encoding Immunogenic Fragments of a VEGF Receptor and Evaluation Therefor in a BALB/c Mouse Model Animals, Bacterial strains, and cell lines: Female BALB/c mice were purchased from the Jackson Laboratory. All animal experiments were performed according to the National Institutes of Health Guide for the Care and Use of Laboratory Animals. The murine D2F2 breast cancer cell line was kindly provided by Dr. W-Z. Wei (Karmanos Cancer Institute, Detroit, Mich., USA). The murine colon carcinoma cell line CT-26 was provided by Dr. I. J. Fidler (MD Anderson Cancer Center, Houston, Tex.). The murine high endothelial venule cell line (HEVc) was a gift from Dr. J. M. Cook-Mills (University of Cincinnati, Ohio, USA). The HEVc-Flk-1 cell line was established by retroviral transduction with the Flk-1 gene by Drs. Harald Wodrich and Andreas G. Niethanmuer. The doubly attenuated *S. typhimurium* (AroA-, dam-) strain RE88 was kindly provided by Remedyne Corporation (Santa Barbara, Calif.) and was transduced with DNA vaccine plasmids to serve as a vaccine carrier, as described above.

Construction of Expression Vectors. Vector construction is illustrated schematically by FIG. 12, Panel A. The expression vectors were established based on the pcDNA/Myc/His vector (Invitrogen, Carlsbad, Calif.) containing the ubiquitin sequence. The peptides were cloned downstream of ubiquitin, and the sequence of each peptide is indicated in Table 6. All peptides were engineered to be in-frame with the myc epitope. Constructs were confirmed by DNA sequencing at The Scripps Research Institute's Core Facility (La Jolla, Calif.). Peptide expression was demonstrated by Western blotting analysis of transfected 293T cells with monoclonal anti-myc antibody (Invitrogen). Once peptide expression was verified, a stop codon was introduced immediately in front of the myc epitope sequences. The resulting vectors, pDd, pKd, pDd+Kd1, and pKd+Dd2 were each verified by nucleotide sequencing and used to transform doubly attenuated *S. typhimurium* (dam-, AroA-) for subsequent immunization.

TABLE 6

Immunogenic Flk Fragments.

| Peptide Name | Sequence | SEQ ID NO: | Included in vaccine |
|---|---|---|---|
| Flk$_{54}$ | RGQRDLDWL | 7 | pDd; pDd + Kd1 |
| Flk$_{210}$ | TYQSIMYIV | 8 | pKd; pKd + Dd2 |

TABLE 6-continued

Immunogenic Flk Fragments.

| Peptide Name | Sequence | SEQ ID NO: | Included in vaccine |
|---|---|---|---|
| $Flk_{221}$ | VGYRIYDVI | 9 | pDd; pKd + Dd2 |
| $Flk_{366}$ | WYRNGRPIE | 10 | pKd; pDd + Kd1 |
| $Flk_{438}$ | QYGTMQTLT | 11 | pKd; pKd + Dd2 |
| $Flk_{741}$ | LGCARAETL | 12 | pDd; pDd + Kd1 |
| $Flk_{792}$ | EGELKTGYL | 13 | pDd; pKd + Dd2 |
| $Flk_{993}$ | LYKDFLYTE | 14 | pKd; pDd + Kd1 |
| $Flk_{1147}$ | QRPSFSELV | 15 | pDd; pDd + Kd1 |
| $Flk_{1153}$ | ELVEHLGNL | 16 | pKd; pKd + Dd2 |

Oral Immunization and Tumor Cell Challenge. Groups of BALB/c mice were immunized 3 times at 1-week intervals by gavage with 100 µl PBS containing approximately $5 \times 10^8$ CFU of RE88 S. typhimurium harboring either empty vector, pDd, pKd, pDd+Kd1 and pKd+Dd2 plasmids. Mice were challenged i.v. with different carcinoma cell lines 2 weeks after the last immunization.

Cytotoxicity Assay. Cytotoxicity was measured by a standard $^{51}Cr$-release assay as previously described (Zhou, H. et al. J. Clin. Invest., 2004; 113: 1792-1798). The percentage of specific target cell lysis was calculated by the formula [(E−S)/(T−S)]×100, where E is the average experimental release, S is the average spontaneous release, and T is the average total release.

Evaluation of anti-angiogenic activity. Suppression of angiogenesis was determined by the Matrigel assay as previously described (Niethammer et al. Nat. Med., 2002, 8: 1369-1375). Vessel growth in the Matrigel was determined with fluorimetry by staining the endothelium using FITC-labeled isolectin B4.

Statistical Analysis. The statistical significance of differential findings between experimental groups and controls was determined by Student's t test. Findings were regarded as significant, if two-tailed P values were <0.05.

Results.

Minigenes encoded by expression vectors are expressed in mammalian cells. As shown in the previous examples, a DNA composition encoding the entire murine Flk-1 gene effectively induced CD8 T cell-mediated anti-angiogenesis that protected mice from tumor cell challenges. This example demonstrates that DNA compositions encoding an immunogenic fragment of a VEGF receptor also elicit an effective antitumor response. Five peptides were included in H-2 Dd- or H-2 Kd-restricted minigenes based on the binding predicted for these MHC class I molecules by the HLA Peptide Binding Predictions program provided by the BioInformatics & Molecular Analysis Section (BIMAS) of NIH, website. The amino acid sequences of these peptides are listed in Table 6.

Figure 12:
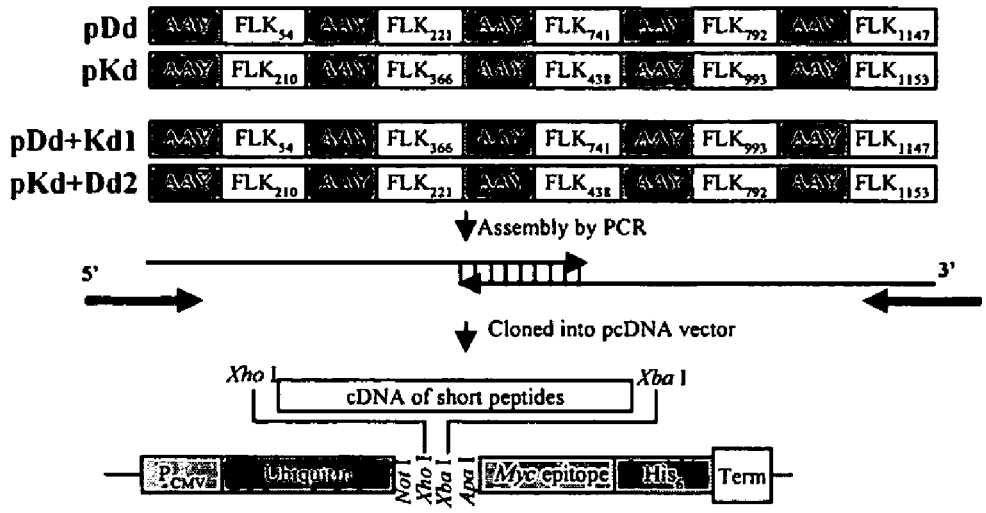
FIG. 12. (A) Schematic map: Minigenes encoding the murine H-2 Dd- and Kd-restricted Flk-1 nonapeptides and spacers were assembled by PCR with overlapping oligonucleotides as templates. The PCR fragments generated were cloned downstream of ubiquitin in a modified pcDNA expression vector by using Xho I and Xba I restriction sites. (B) Proteins encoded by minigenes were expressed in mammalian cells. 293T cells were transfected separately with either pDd-myc, pDd+Kd1-myc, pKd-myc or pKd+Dd2-myc for 24 hours, harvested, lysed and analyzed by Western blotting with anti-myc monoclonal antibody.

Expression vectors were constructed based on the backbone of pcDNA/myc/His (FIG. 12, Panel A) that was modified to encode ubiquitin. Ubiquitin is useful for effective antigen processing in the proteasome leading to efficacious minigene vaccines. Gene expression of the resulting plasmids was verified by Western blotting analysis of 293T cells transfected with either pDd-myc, pDb+Kd1-myc, pKd-myc or pKd+Dd2-myc. As expected, 293T cells transfected with pKd-myc or pKd+Dd2-myc plasmid displayed two major bands of approximately 12 and 21 Kda, corresponding to non-ubiquitinated or ubiquitinated polypeptides, respectively (FIG. 12, Panel B). However, Western Blot analysis of 293T cells transfected with pDd-myc and pDd+Kd1-myc showed bands of slightly higher molecular weight with the upper band being a doublet. Since these plasmids contain the correct nucleotide sequences, this phenomenon is indicative of post-translational modification, likely glycosylation. According to glycosylation prediction based on the program provided by Center for Biological Sequence Analyses at the Technical University of Denmark (DTU), website, the $S_{1150}$ and $S_{1152}$ amino acid residues in the $Flk_{1147}$ peptide (Table 6), which were included in the pDd-myc and pDd+Kd1-myc vectors, are most likely to be glycosylated, with $S_{1152}$ being almost 10 times more likely to be glycosylated than all other residues encoded by these minigenes.

The vectors pDd, pKb, pDd+Kd1 and pKd+Dd2 were generated by introducing a stop codon immediately downstream from the peptide coding sequences, so that the translated protein would not contain the myc epitope. The correct constructs were confirmed by DNA sequencing. The empty pcDNA vector was also included for control purposes, since previous data indicated that vectors containing only ubiquitin did not induce any tumor protective immune responses.

Figure 13:
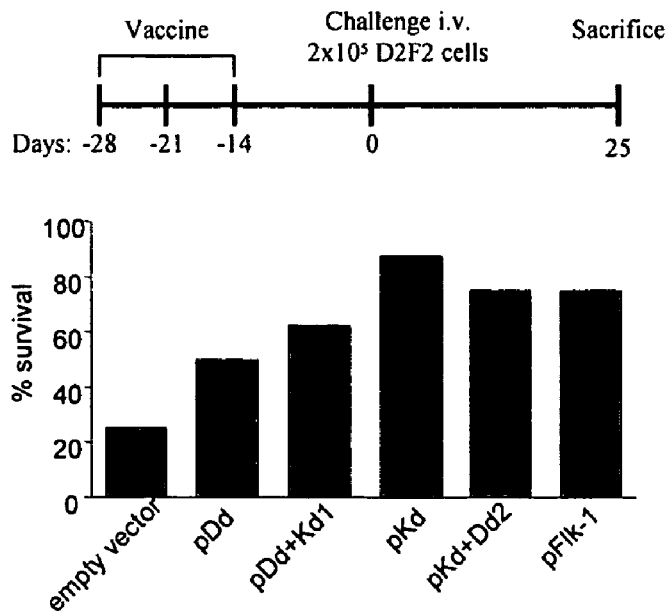
FIG. 13. Top panel: Schematic of experimental protocol. Lower panel: Survival rate of mice 25 days after tumor cell challenge. The Flk-1 whole gene vaccine was used as positive control. Groups of BALB/c mice (n=8) were immunized 3 times at 1 week intervals with attenuated *Salmonella typhimurium* RE-88 harboring the vectors indicated. Mice were challenged 2 weeks after the last immunization by i.v. injection of $2\times10^5$ D2F2 breast carcinoma cells.

The minigene vaccines protect mice against tumors of different origin. Initially, the minigene DNA vaccines were tested in a breast carcinoma model, where mice were first vaccinated with the minigene vaccines and then challenged i.v. with murine D2F2 breast carcinoma cells (FIG. 13, upper panel). In the empty vector control group, only 25% of the mice survived 25 days after tumor cell challenge (FIG. 13). In contrast, the survival rate was 50% and 62.5% in pDd and pDd+Kd1 vaccinated groups, respectively. More importantly, the survival rate improved to 82.5% and 75% in pKd and pKd+Dd2 vaccinated groups of mice, respectively. This is quite comparable to the 75% survival rate which was observed in groups of mice immunized with the whole Flk-1 gene vaccine (FIG. 13).

Figure 14:
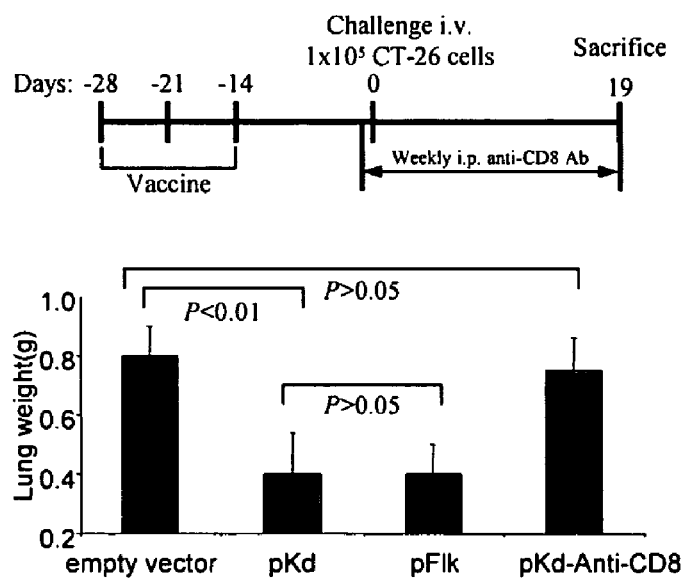
FIG. 14. Top panel: Schematic of experimental protocol. Lower panel: Average lung weights of mice from each experimental group 19 days after tumor cell challenge. The average lung weight of normal mice was about 0.2 g. The Flk-1 whole gene vaccine was used as positive control. Groups of BALB/c mice (n=8) were immunized 3 times at 1 week intervals with attenuated *Salmonella typhimurium* harboring the vectors indicated. Mice were challenged 2 weeks after the last immunization by i.v. injection of $1\times10^5$ CT-26 colon carcinoma cells. CD8 depletion was performed by i.p. injections of anti-CD8 antibody (2.43, 0.5 mg/mouse) 1 day before tumor challenge, and repeated weekly injections.

To verify that the minigene vaccine designed for anti-angiogenesis is not merely specific for D2F2 breast carcinoma, its efficacy was also tested in the CT-26 murine colon carcinoma model. In this case, this pKd minigene also decreased the tumor load by 60% (FIG. 14). Similar results were also obtained by using full-length Flk-1 DNA vaccine (FIG. 14). Taken together, these data demonstrate that Flk-1 minigene vaccines also elicit protections against tumors of different origin in syngeneic BALB/c mice.

The minigene vaccines induce a CTLs response which is capable of killing Flk-1$^+$ endothelial cells. To identify the effector cell population responsible for the vaccine induced tumor protection, in vivo depletion experiments were performed. CD8 T cells were depleted by i.p. injection of 0.5 mg/mouse 2.43 anti-CD8 monoclonal antibody 1 day before tumor cell challenge and repeated weekly (FIG. 14, upper panel). The depletion of CD8 T cells completely abrogated the pKd minigene-induced tumor protection (FIG. 14), indicating that CD8 T cells are the major effector cells.

Figure 15:
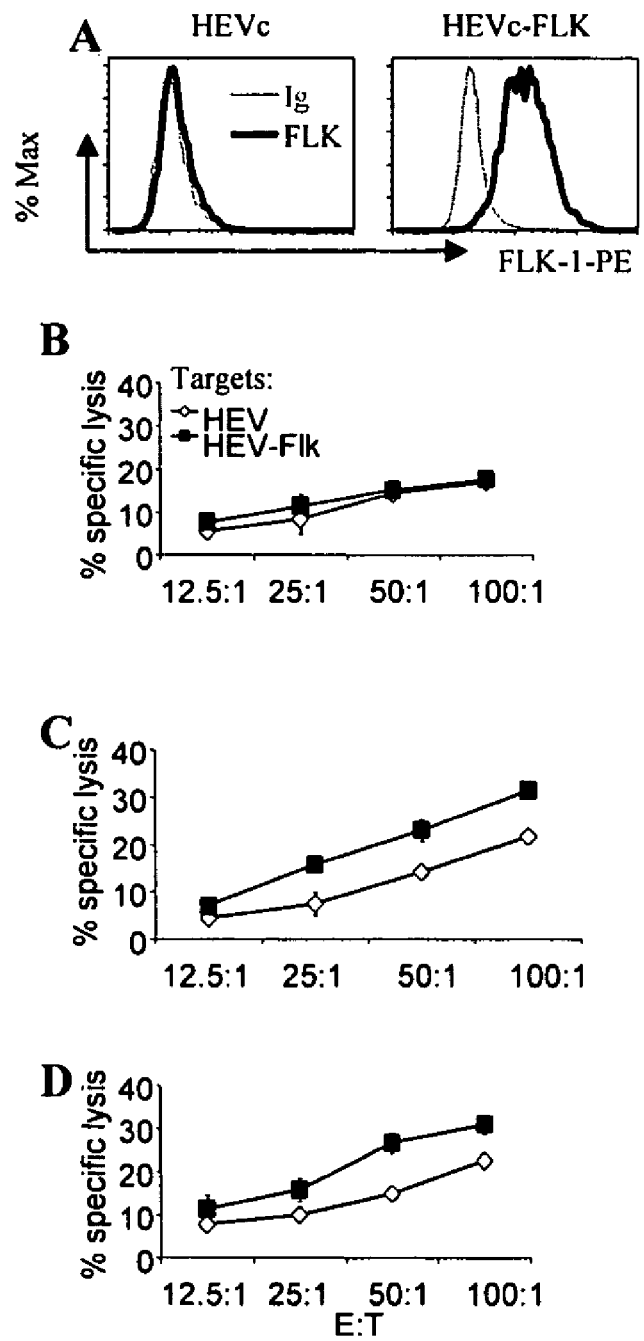
FIG. 15. (A) Surface expression of Flk-1 by the endothelial cell line HEVc and by HEVc cells stably transfected with Flk-1 (HEVc-Flk). Cells were washed and incubated with PE-conjugated isotype control Ab (thin grey lines), or PE-conjugated anti-Flk-1 Ab (thick black lines). Groups of immunized BALB/c mice (n=4) were sacrificed 2 weeks after the last immunization and splenocytes isolated from them were stimulated with irradiated HEVc-Flk cells for 5 days. Thereafter, cytotoxicity assays were performed with parental HEVc (◇) or HEVc-Flk (■) as target cells. (B) Effector cells isolated from control group of mice immunized only with empty vector. (C) Effector cells from the pKd vaccinated group of mice. (D) Effector cells from the positive control group immunized with the Flk-1 whole gene vaccine.

Cytotoxicity assays were employed to demonstrate CTL activity of immunized mice. The target cells used were the murine endothelial cell line HEVc, and this same cell line stably transfected with Flk-1 plasmid (HEVc-Flk). Wild-type HEVc cells are Flk-, whereas HEVc-Flk cells readily express Flk-1 on the surface as indicated by flow cytometry analysis (FIG. 15, Panel A). Splenocytes isolated from empty vector control mice showed similar killing of HEVc-Flk cell as of HEVc parental cells (FIG. 15, Panel B). However, splenocytes from pKd-vaccinated mice induced significantly stronger killing against Flk$^+$ target cells (FIG. 15, Panel C). This killing capacity is very similar to that of splenocytes isolated from mice immunized with the whole Flk-1 gene vaccine (FIG. 15, Panel D). These data demonstrate the specificity of the pKd minigene vaccine-induced CTL activity and its capacity to kill Flk-1$^+$ proliferating endothelial cells.

The pKd minigene vaccine induced anti-angiogenesis effects. In an effort to investigate whether anti-angiogenesis played a key role in pKd-vaccine-induced tumor protection, tumor sections from immunized and control mice were analyzed by Masson's trichrome staining. Tumor sections from empty vector control group mice showed ample, multiple blood vessels within the tumor mass. In contrast, blood vessels were rather scarce in tumor sections from pKd-vaccinated mice (FIG. 16, Panel A). These data demonstrate that immunization with the pKd vaccine resulted in the reduction of tumor vasculature.

Matrigel assays were also performed, in which blood vessel formation within the Matrigel was induced by recombinant bFGF. The difference in vessel formation was quantified by measuring the relative fluorescence intensity of extracts from Matrigel plugs obtained from immunized or control mice. Thus mice vaccinated with pKd vaccine displayed a reduction in average relative fluorescence (FIG. 16, Panel B). Taken together, these findings demonstrate that the pKd minigene vaccine induced marked anti-angiogenic effects, which aided in the protection of BALB/c mice from challenge with tumor cells of different origin in a prophylactic setting.

EXAMPLE 6

DNA Composition Encoding Immunogenic Fragments of a VEGF Receptor and Evaluation Therefor in a C57BL/6J Mouse Model Animals, bacterial strains, and cell lines. Male or female C57BL/6J mice were purchased from the Jackson Laboratory (Bar Harbor, Me.). All animal experiments were performed according to the National Institutes of Health Guides for the Care and Use of Laboratory Animals, and all protocols were approved by the Institutional Animal Care and Use Committee of The Scripps Research Institute.

The murine lung carcinoma cell line D121 was provided by Dr. L. Eisenbach (Weizmann Institute of Science, Rehovot, Israel). The murine prostate cancer cell line RM9 was obtained from Dr. T. C. Thompson (Baylor College of Medicine, Houston, Tex.). The murine breast cancer cell line EO771 was made available by Dr. D. Ross (University of Kentucky, Louisville, Ky.). Murine endothelial cell line, MS1, was purchased from the American Type Culture Collection (ATCC; Manassas, Va.). All cell lines were cultured in Dulbecco's modified Eagle medium (DMEM) (Invitrogen, Grand Island, N.Y.), supplemented with 10% (vol/vol) fetal bovine serum (FBS).

The double-attenuated $S.$ $typhimurium$ (AroA$^-$, dam$^-$) strain RE88 was provided by the Remedyne Corporation (Santa Barbara, Calif.), and was transformed with DNA vaccine plasmids as described above.

Figure 17:
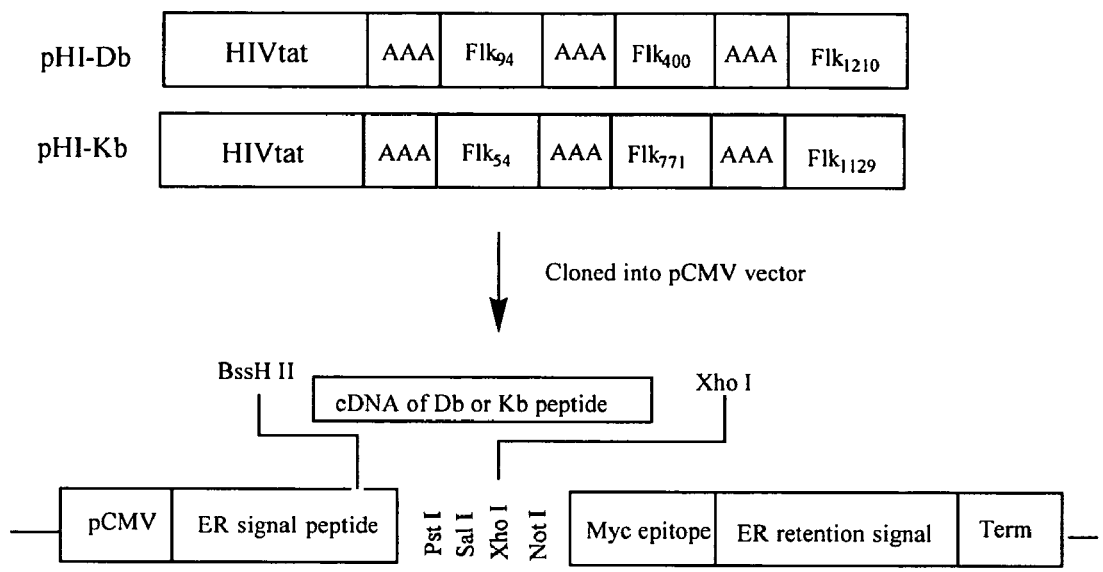
FIG. 17 illustrates minigenes encoding the murine pHI-Dd and pHI-Kb, which comprise immunogenic Flk-1 peptide fragments separated by AAA spacers, and including a HIVtat peptide at the N-terminus thereof. Vectors were assembled by PCR with overlapping oligonucleotides as templates as shown in the figure.

Construction of Expression Vectors. The expression vector pCMV/ER/Myc was purchased from Invitrogen (Carlsbad, Calif.). Vector construction is illustrated schematically in FIG. 17. The following expression vectors were constructed: pHI-myc, pHI-Db-myc, pHI-Kb-myc (See FIG. 17), where the HIVtat peptide (HI) represents RKKRRQRRR (SEQ ID NO: 17). The Flk$_{94}$, Flk$_{400}$, and Flk$_{1210}$ peptides stand for RVVGNDTGA (SEQ ID NO: 18), VILTNPISM (SEQ ID NO: 19), and FHYDNTAGI (SEQ ID NO: 20), respectively. Flk$_{54}$, Flk$_{771}$, and Flk$_{1129}$ peptides are designated for RGQRDLDWL (SEQ ID NO: 21), VIAMFFWLL (SEQ ID NO: 22), and TTPEMHYQTM (SEQ ID NO: 23), respectively. All peptides were engineered to be in-frame with the myc epitope. Constructs were confirmed by DNA sequencing at The Scripps Research Institute's Core Facility (La Jolla, Calif.). Peptide expression was demonstrated by Western blotting with monoclonal antibody (Invitrogen, Carlsbad, Calif.). Once peptide expression was verified, a stop codon was introduced immediately in front of the myc epitope sequences. The resulting vectors, namely pHI, pHI-Db, and pHI-Kb, were verified by nucleotide sequencing and use to transform double-attenuated $S$ $typhimurium$ (dam-, AroA-) for immunization. The pCMV empty vector was also included in the experiments as a control.

Peptide Synthesis. All peptides were synthesized with more than 95% purity by high-performance liquid chromatography (HPLC) by Multiple Peptide Systems (San Diego, Calif.).

Oral Immunization and Tumor-Cell Challenge. Groups of C57BL/6J mice were immunized 3 times at 1-week intervals by gavage with 100 μL phosphate-buffered saline (PBS) containing approximately $5 \times 10^8$ double-attenuated RE88 $S.$ $typhimurium$ harboring either pCMV, pHI, pHI-Db, or pHI-Kb plasmids. Mice were challenged intravenously with different carcinoma cells 2 weeks after the last immunization.

Cytotoxicity and ELISPOT assays and in vivo depletion. Cytotoxicity was measured by a standard $^{51}$Cr-release assay as described above. The percentage of specific target cell lysis was calculated by the formula $[(E-S)/(T-S)] \times 100$, where E is the average experimental release, S the average spontaneous release, and T the average total release.

Enzyme-linked immunospot (ELISPOT) assays were performed with an ELISPOT kit (PharMingen, La Jolla, Calif.) according to the instructions provided by the manufacturer.

In vivo depletion was performed on vaccinated mice by intraperitoneal injection of anti-CD4 antibody (GK1.5, 0.4 mg/mouse) or anti-CD8 antibody (2.43, at 0.6 mg/mouse) 1 day before tumor challenge and repeated weekly.

Evaluation of Antiangiogenic Effects. Two weeks after the last vaccination, mice were given subcutaneous injections in the sternal region with 400 μL growth factor-reduced Matrigel (BD Biosciences, San Jose, Calif.) containing 400 ng/mL basic fibroblast growth factor (PeproTech, Rocky Hill, N.J.). In all mice, the endothelium was stained 6 days later by intravenous injection of 200 μL fluorescent $Bandeiraea$ $simplicifolia$ lectin I, isolectin B4 at 0.1 mg/mL (Vector Laboratories, Burlingame, Calif.). Fifteen minutes later, the Matrigel plugs were excised and evaluated by confocal microscopy (Axiovert 100TV microscope; Carl Zeiss, Oberkochem, Germany; 40×/1.3 NA objective; and SPOT camera and software), and then lectin-fluorescein isothiocyanate (FITC) was extracted with RIPA lysis buffer (0.15 mM NaCl/0.05 mM Tris [tris(hydroxymethyl)aminomethane]-HCl, pH 7.2/1% Triton X-100/1% sodium deoxycholate/0.1% sodium dodecyl sulfate) from 100-μg Matrigel plugs, to be quantified by fluorometry at 490 nm.

Statistical analysis. The statistical significance of differential findings between experimental groups and controls was determined by the Student t test. Findings were regarded as significant when 2-tailed P was less than 0.05.

Results.

Minigenes encoded by expression vectors are expressed in mammalian cells. As demonstrated above, a DNA vaccine encoding the entire murine Flk-1 gene effectively induced CD8$^+$ T cell-mediated antiangiogenesis that protected mice from tumor-cell challenge. Here, a minigene approach was utilized to demonstrate that Flk-1 epitopes can induce similar antiangiogenic responses as the whole Flk-1 gene vaccine in a C57BL/6J mouse model. To this end, 3 peptides were included in H-2D$^b$- or H-2 K$^b$-restricted minigenes based on the binding predicted for these MHC class I molecules using the HLA Peptide Binding Predictions program provided at the www website of the BioInformatics & Molecular Analysis Section (BIMAS) of the National Institutes of Health (NIH).

Expression vectors were constructed based on the backbone of pCMV/ER/Myc as described above. A HIVtat peptide (RKKRRQRRR, SEQ ID NO: 17), one of the commonly used membrane-translocating peptides, was also included in the minigene vaccine to facilitate the delivery of the encoded peptides. After transfection of 293T cells with either pHI-myc, pHI-Dd-myc, or pHI-Kb-myc, correct expression of these constructs was demonstrated by Western blotting, which revealed single bands with the expected molecular mass of 15 kDa. The mature peptides did not contain the myc epitope because the vaccine vectors pHI, pHI-Db and pHI-Kb were generated by introducing a stop codon immediately downstream from the peptide-coding sequences. The correct vector constructs were confirmed by DNA sequencing. The empty pCMV vector was also included for control purposes.

The pHI-Db minigene vaccine protects mice against tumors of different origin by inducing immune responses that suppress tumor angiogenesis. Initially, the minigene DNA vaccines were evaluated in a prophylactic lung cancer model, where mice were first vaccinated with a minigene vaccine and then challenged intravenously with D121 lung carcinoma cells. In this case, the pHI-Db minigene elicited the best tumor protection, with 62.5% of mice surviving 75 days after tumor cell challenge. In contrast, none of the mice in the pCMV control group survived. The pHI or pHI-Kb vaccines induced only some tumor protection, however, with 25% of the mice surviving 75 days after tumor challenge.

To verify that the minigene vaccine effectively protects mice from tumors of different origins, the vaccine efficacy was also tested in a RM9 prostate carcinoma model. In this case, the pHI-Db minigene also protected the mice from RM9 tumor cell challenge indicating that the pHI-Db vaccine induces suppression of metastases independent of the tumor type.

In vivo depletion assays were performed to identify the cell population responsible for the tumor protection effects. Depletion of CD8$^+$ cells completely abrogated the vaccine-induced protection, whereas the depletion of CD4$^+$ cells moderately enhanced the protection against tumor challenge, indicating that the CD8$^+$ T cells are the major effectors.

The specificity of the CTL responses was further investigated in $^{51}$Cr-release assays. The pHI-Db vaccine induced a specific cytotoxic response against a Flk-1$^+$ endothelial cell line MS1, but not against Flk-1$^-$RM9 prostate carcinoma cells. These results indicate that the cytotoxic response induced by the pHI-Db vaccine was indeed directed against endothelial cells, presumably specific for Flk-1, rather than against tumor cells. This finding also provides evidence that the pHI-Db minigene vaccine would induce an antiangiogenic response in vivo.

Matrigel assays were also performed, which indicated that vaccination with minigene pHI-Db indeed suppressed vascularization. This was clearly demonstrated by reduced blood vessel formation observed in representative Matrigel plugs after in vivo staining of the endothelium with FITC-conjugated lectin. This difference in vessel formation was also demonstrated quantitatively by measuring the average relative fluorescence. Taken together, these findings demonstrate that the pHI-Db minigene vaccine induced antiangiogenic effects, which protected mice from challenge with tumor cells of different origin.

The pHI-Db Vaccine Induces a Flk$_{400}$-Specific Immune Response. To evaluate each of the 3 immunogenic Flk-1 peptide fragments encoded by the pHI-Db minigene, splenocytes isolated from mice immunized with pHI-Db were analyzed by ELISPOT assays using individual synthetic peptides as stimulators. A specific Flk$_{400}$ response was detected only in the pHI-Db-vaccinated group of mice, whereas no significant Flk$_{94}$- or Flk$_{1210}$-specific responses were found in any of the experimental groups of mice, suggesting that Flk$_{400}$ is the major epitope recognized by CTL effector cells.

To further confirm this observation, splenocytes from vaccinated mice were stimulated with synthetic peptides for 5 days and tested against MS1 and RM9 target cells in cytotoxicity assays. Only Flk$_{400}$-stimulated splenocytes exhibited specific cytotoxic killing against Flk-1$^+$ MS1 target cells, but revealed almost no killing of Flk-1$^-$ RM9 tumor cells. Splenocytes stimulated with Flk$_{94}$ induced low levels of MS1-specific killing whereas Flk$_{1210}$-stimulated splenocytes mainly displayed low levels of nonspecific killing, confirming the dominance of the Flk$_{400}$ epitope within the minigene vaccine.

When peptide-stimulated splenocytes isolated from pHI-Db-vaccinated mice were restimulated twice more in vitro with irradiated, peptide-loaded splenocytes every 7 days, and then tested again for their cytotoxicity, only those cells restimulated with Flk$_{400}$-loaded splenocytes showed greatly enhanced cytotoxicity, resulting in a higher percent specific killing at a much lower effector-target (E/T) ratio. In contrast, such restimulation with Flk$_{94}$-loaded splenocytes resulted in a lower level of MS1-specific killing, whereas cells restimulated with Flk$_{1210}$-loaded splenocytes failed to induce any significant killing. Taken together, these findings indicate that restimulation with Flk$_{400}$-loaded splenocytes enriches the CTL population that specifically targets Flk-1$^+$ endothelial cells.

The tumor protective ability of a minigene vaccine encoding only Flk$_{400}$ in the absence of Flk$_{94}$ and Flk$_{1210}$ was assessed and compared with the effect of the pHI-Db minigene vaccine in a EO771 breast carcinoma model. EO771 cells do not express Flk-1, but express surface H-2D$^b$ as detected by flow cytometry. In fact, both pHI-Db and pHI-Flk$_{400}$ minigene vaccines significantly protected the mice against EO771 tumor cell challenge to an extent comparable to the protection induced by the DNA vaccine of Example 1 encoding the entire Flk-1 gene. The pHI-Db vaccine also achieved similar efficacy as Flk-1 whole-gene vaccine in RM9 prostate and D121 lung carcinoma models.

Long-term protection was established by the pHI-Db minigene vaccine, as well. At 10 months after their last vaccination, pHI-Db-vaccinated mice showed significantly reduced lung metastases after intravenous challenging with EO771 breast carcinoma cells, an Flk$_{400}$-specific T cells could still be detected in the spleen of these mice.

The DNA Vaccine Encoding the Entire Flk-1 Gene Induces a Flk$_{400}$-specific CTL Response. The Flk$_{400}$-specific response was also induced by a DNA vaccine encoding the entire Flk-1 gene. Such responses were detected in splenocytes freshly isolated from pFlk-1-vaccinated mice as demonstrated by ELISPOT assays. These splenocytes maintained the specificity of the responses after in vitro stimulation with Flk$_{400}$ peptides. However, controls were negative, because stimulation with Flk$_{94}$ had no effect when compared to non-stimulated cells. Only nonspecific activation resulted from stimulation with Flk$_{1210}$. Moreover, splenocytes isolated from pFlk-1-vaccinated mice also displayed preferential cytotoxic killing of EO771 tumor cells loaded with Flk$_{400}$ as compared to the killing of unloaded EO771 cells. Similar results were also observed in pHI-Db-vaccinated mice, which were used as a positive control. The killing of EO771 or Flk$_{400}$-loaded EO771 tumor cells was largely indistinguishable in pCMV or pHI control groups. Taken together, these findings strongly indicate that the DNA vaccine encoding the entire Flk-1 gene was capable of inducing a $Flk_{400}$-specific immune response.

Numerous variations and modifications of the embodiments described above can be effected without departing from the spirit and scope of the novel features of the invention. It is to be understood that no limitations with respect to the specific embodiments illustrated herein are intended or should be inferred. It is, of course, intended to cover by the appended claims all such modifications as fall within the scope of the claims.

We claim:

1. A DNA composition comprising a DNA construct encoding at least one immunogenic fragment of a VEGF receptor capable of eliciting an immune response against vascular endothelial cells, which is expressible in immune cells, and is incorporated in a pharmaceutically acceptable carrier;

wherein the DNA construct is incorporated in an attenuated bacterial vector.

2. The DNA composition of claim 1 wherein the attenuated bacterial vector is selected from attenuated *Salmonella typhimurium, Salmonella typhi, Shigella, Bacillus, Lactobacillus, BCG, Escherichia coli, Vibrio cholerae*, and *Campylobacter*.

3. A DNA composition comprising a DNA construct encoding at least one immunogenic fragment of a VEGF receptor capable of eliciting an immune response against vascular endothelial cells, which is expressible in immune cells, and is incorporated in a pharmaceutically acceptable carrier wherein the DNA construct is incorporated in an attenuated bacterial vector, AroA$^-$, dam$^-$ *Salmonella typhimurium*.

4. A DNA composition comprising a DNA construct encoding at least one immunogenic fragment of a VEGF receptor capable of eliciting an immune response against vascular endothelial cells, which is expressible in immune cells, and is incorporated in a pharmaceutically acceptable carrier wherein the composition further comprises a DNA construct encoding an immune effector protein expressible in immune cells.

5. The DNA composition of claim 4 wherein the immune effector protein is a cytokine.

6. The DNA composition of claim 5 wherein the cytokine is CCL21, IL-2, or CD40LT.

7. The DNA composition of claim 1 wherein the immunogenic fragment of a VEGF receptor comprises at least one immunogenic VEGF receptor fragment consisting of about 8 to 10 consecutive amino acid residues of Flk-1 (SEQ ID NO: 6).

* * * * *

UNITED STATES PATENT AND TRADEMARK OFFICE
CERTIFICATE OF CORRECTION

PATENT NO. : 8,048,428 B2
APPLICATION NO. : 11/507298
DATED : November 1, 2011
INVENTOR(S) : Reisfeld et al.

Page 1 of 1

It is certified that error appears in the above-identified patent and that said Letters Patent is hereby corrected as shown below:

In the Specification

Column 1, Lines 12-19, the paragraph GOVERNMENTAL RIGHTS should be changed to:
-- STATEMENT OF GOVERNMENT LICENSE RIGHTS
This invention was made with government support under grants CA083856 and CA115751 awarded by the National Institutes of Health and grants DAMD17-02-1-0137 and DAMD17-02-1-0562 awarded by the Army Medical Research and Materiel Command. The government has certain rights in the invention. --

Signed and Sealed this
Thirty-first Day of March, 2020

Andrei Iancu
*Director of the United States Patent and Trademark Office*

SEQUENCE LISTING

<160> NUMBER OF SEQ ID NOS: 23

<210> SEQ ID NO 1
<211> LENGTH: 4071
<212> TYPE: DNA
<213> ORGANISM: human

<400> SEQUENCE: 1

| | | | | | |
|---|---|---|---|---|---|
| atggagagca | aggtgctgct | ggccgtcgcc | ctgtggctct | gcgtggagac | ccgggccgcc | 60 |
| tctgtgggtt | tgcctagtgt | ttctcttgat | ctgcccaggc | tcagcataca | aaaagacata | 120 |
| cttacaatta | aggctaatac | aactcttcaa | attacttgca | ggggacagag | ggacttggac | 180 |
| tggctttggc | ccaataatca | gagtggcagt | gagcaaaggg | tggaggtgac | tgagtgcagc | 240 |
| gatggcctct | tctgtaagac | actcacaatt | ccaaaagtga | tcggaaatga | cactggagcc | 300 |
| tacaagtgct | tctaccggga | aactgacttg | gcctcggtca | tttatgtcta | tgttcaagat | 360 |
| tacagatctc | catttattgc | ttctgttagt | gaccaacatg | gagtcgtgta | cattactgag | 420 |
| aacaaaaaca | aaactgtggt | gattccatgt | ctcgggtcca | tttcaaatct | caacgtgtca | 480 |
| ctttgtgcaa | gatacccaga | aaagagattt | gttcctgatg | gtaacagaat | ttcctgggac | 540 |
| agcaagaagg | gctttactat | tcccagctac | atgatcagct | atgctggcat | ggtcttctgt | 600 |
| gaagcaaaaa | ttaatgatga | aagttaccag | tctattatgt | acatagttgt | cgttgtaggg | 660 |
| tataggattt | atgatgtggt | tctgagtccg | tctcatggaa | ttgaactatc | tgttggagaa | 720 |
| aagcttgtct | taaattgtac | agcaagaact | gaactaaatg | tggggattga | cttcaactgg | 780 |
| gaataccctt | cttcgaagca | tcagcataag | aaacttgtaa | accgagacct | aaaaacccag | 840 |
| tctgggagtg | agatgaagaa | attttttgagc | accttaacta | tagatggtgt | aacccggagt | 900 |
| gaccaaggat | tgtacacctg | tgcagcatcc | agtgggctga | tgaccaagaa | gaacagcaca | 960 |
| tttgtcaggg | tccatgaaaa | acctttttgtt | gcttttggaa | gtggcatgga | atctctggtg | 1020 |
| gaagccacgg | tgggggagcg | tgtcagaatc | cctgcgaagt | accttggtta | cccacccca | 1080 |
| gaaataaaat | ggtataaaaa | tggaataccc | cttgagtcca | atcacacaat | taaagcgggg | 1140 |
| catgtactga | cgattatgga | agtgagtgaa | agagacacag | gaaattacac | tgtcatcctt | 1200 |
| accaatccca | tttcaaagga | gaagcagagc | catgtggtct | ctctggttgt | gtatgtccca | 1260 |
| ccccagattg | gtgagaaatc | tctaatctct | cctgtggatt | cctaccagta | cggcaccact | 1320 |
| caaacgctga | catgtacggt | ctatgccatt | cctcccccgc | atcacatcca | ctggtattgg | 1380 |
| cagttggagg | aagagtgcgc | caacgagccc | agccaagctg | tctcagtgac | aaacccatac | 1440 |
| ccttgtgaag | aatggagaag | tgtggaggac | ttccagggag | gaaataaaat | tgaagttaat | 1500 |
| aaaaatcaat | ttgctctaat | tgaaggaaaa | aacaaaaactg | taagtaccct | tgttatccaa | 1560 |
| gcggcaaatg | tgtcagcttt | gtacaaatgt | gaagcggtca | caaagtcgg | gagaggagag | 1620 |
| agggtgatct | ccttccacgt | gaccagggg | cctgaaatta | ctttgcaacc | tgacatgcag | 1680 |
| cccactgagc | aggagagcgt | gtcttttgtgg | tgcactgcag | acagatctac | gtttgagaac | 1740 |
| ctcacatggt | acaagcttgg | cccacagcct | ctgccaatcc | atgtgggaga | gttgcccaca | 1800 |

```
cctgtttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatcccgt ggatctgaaa   2880 cggcgcttgg acagcatcac cagtagccag agctcagcca gctctggatt tgtggaggag   2940
aagtccctca gtgatgtaga agaagaggaa gctcctgaag atctgtataa ggacttcctg   3000
accttggagc atctcatctg ttacagcttc caagtggcta agggcatgga gttcttggca   3060
tcgcgaaagt gtatccacag ggacctggcg gcacgaaata tcctcttatc ggagaagaac   3120
gtggttaaaa tctgtgactt tggcttggcc cgggatattt ataaagatcc agattatgtc   3180
agaaaaggag atgctcgcct cccctttgaaa tggatggccc cagaaacaat ttttgacaga   3240
gtgtacacaa tccagagtga cgtctggtct tttggtgttt tgctgtggga aatattttcc   3300
ttaggtgctt ctccatatcc tggggtaaag attgatgaag aattttgtag gcgattgaaa   3360
gaaggaacta gaatgagggc ccctgattat actacaccag aaatgtacca gaccatgctg   3420
gactgctggc acggggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgtttcc   3600
tgtatggagg aggaggaagt atgtgacccc aaattccatt atgacaacac agcaggaatc   3660
agtcagtatc tgcagaacag taagcgaaag agccggcctg tgagtgtaaa acatttgaa   3720 gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg aatggtgcc cagcaaaagc agggagtctg tggcatctga aggctcaaac   3900
cagacaagcg gctaccagtc cggatatcac tccgatgaca cagacaccac cgtgtactcc   3960
agtgaggaag cagaactttt aaagctgata gagattggag tgcaaaccgg tagcacagcc   4020
cagattctcc agcctgactc ggggaccaca ctgagctctc ctcctgttta a            4071
```

<210> SEQ ID NO 2
<211> LENGTH: 1356
<212> TYPE: PRT
<213> ORGANISM: human

<400> SEQUENCE: 2

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

-continued

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
            405                 410                 415

Val Tyr Val Pro Pro Gln Ile Gly Glu Lys Ser Leu Ile Ser Pro Val
        420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
            645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
            725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
        755                 760                 765

Val Gly Thr Ala Val Ile Ala Met Phe Phe Trp Leu Leu Leu Val Ile
        770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

-continued

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Ala Pro
            980                 985                 990

Glu Asp Leu Tyr Lys Asp Phe Leu Thr Leu Glu His Leu Ile Cys Tyr
            995                1000                1005

Ser Phe Gln Val Ala Lys Gly Met Glu Phe Leu Ala Ser Arg Lys Cys
            1010                1015                1020

Ile His Arg Asp Leu Ala Ala Arg Asn Ile Leu Leu Ser Glu Lys Asn
1025                1030                1035                1040

Val Val Lys Ile Cys Asp Phe Gly Leu Ala Arg Asp Ile Tyr Lys Asp
            1045                1050                1055

Pro Asp Tyr Val Arg Lys Gly Asp Ala Arg Leu Pro Leu Lys Trp Met
            1060                1065                1070

Ala Pro Glu Thr Ile Phe Asp Arg Val Tyr Thr Ile Gln Ser Asp Val
            1075                1080                1085

Trp Ser Phe Gly Val Leu Leu Trp Glu Ile Phe Ser Leu Gly Ala Ser
            1090                1095                1100

Pro Tyr Pro Gly Val Lys Ile Asp Glu Glu Phe Cys Arg Arg Leu Lys
1105                1110                1115                1120

Glu Gly Thr Arg Met Arg Ala Pro Asp Tyr Thr Thr Pro Glu Met Tyr
            1125                1130                1135

Gln Thr Met Leu Asp Cys Trp His Gly Glu Pro Ser Gln Arg Pro Thr
            1140                1145                1150

Phe Ser Glu Leu Val Glu His Leu Gly Asn Leu Leu Gln Ala Asn Ala
            1155                1160                1165

Gln Gln Asp Gly Lys Asp Tyr Ile Val Leu Pro Ile Ser Glu Thr Leu
            1170                1175                1180

Ser Met Glu Glu Asp Ser Gly Leu Ser Leu Pro Thr Ser Pro Val Ser
1185                1190                1195                1200

Cys Met Glu Glu Glu Glu Val Cys Asp Pro Lys Phe His Tyr Asp Asn
            1205                1210                1215

Thr Ala Gly Ile Ser Gln Tyr Leu Gln Asn Ser Lys Arg Lys Ser Arg
            1220                1225                1230

Pro Val Ser Val Lys Thr Phe Glu Asp Ile Pro Leu Glu Glu Pro Glu
            1235                1240                1245

```
Val Lys Val Ile Pro Asp Asp Asn Gln Thr Asp Ser Gly Met Val Leu
    1250                1255                1260
Ala Ser Glu Glu Leu Lys Thr Leu Glu Asp Arg Thr Lys Leu Ser Pro
1265                1270                1275                1280
Ser Phe Gly Gly Met Val Pro Ser Lys Ser Arg Glu Ser Val Ala Ser
                1285                1290                1295
Glu Gly Ser Asn Gln Thr Ser Gly Tyr Gln Ser Gly Tyr His Ser Asp
                1300                1305                1310
Asp Thr Asp Thr Thr Val Tyr Ser Ser Glu Glu Ala Glu Leu Leu Lys
        1315                1320                1325
Leu Ile Glu Ile Gly Val Gln Thr Gly Ser Thr Ala Gln Ile Leu Gln
    1330                1335                1340
Pro Asp Ser Gly Thr Thr Leu Ser Ser Pro Pro Val
1345                1350                1355

<210> SEQ ID NO 3
<211> LENGTH: 4017
<212> TYPE: DNA
<213> ORGANISM: human

<400> SEQUENCE: 3
```

| | | |
|---|---|---|
| atggtcagct actgggacac cggggtcctg ctgtgcgcgc tgctcagctg tctgcttctc | 60 |
| acaggatcta gttcaggttc aaaattaaaa gatcctgaac tgagtttaaa aggcacccag | 120 |
| cacatcatgc aagcaggcca gacactgcat ctccaatgca ggggggaagc agcccataaa | 180 |
| tggtctttgc ctgaaatggt gagtaaggaa agcgaaaggc tgagcataac taaatctgcc | 240 |
| tgtggaagaa atggcaaaca attctgcagt actttaacct tgaacacagc tcaagcaaac | 300 |
| cacactggct tctacagctg caaatatcta gctgtaccta cttcaaagaa gaaggaaaca | 360 |
| gaatctgcaa tctatatatt tattagtgat acaggtagac cttttcgtaga gatgtacagt | 420 |
| gaaatccccg aaattataca catgactgaa ggaagggagc tcgtcattcc ctgccgggtt | 480 |
| acgtcaccta acatcactgt tactttaaaa aagtttccac ttgacacttt gatccctgat | 540 |
| ggaaaacgca taatctggga cagtagaaag ggcttcatca tatcaaatgc aacgtacaaa | 600 |
| gaaatagggc ttctgacctg tgaagcaaca gtcaatgggc atttgtataa gacaaactat | 660 |
| ctcacacatc gacaaaccaa tacaatcata gatgtccaaa taagcacacc acgcccagtc | 720 |
| aaattactta gaggccatac tcttgtcctc aattgtactg ctaccactcc cttgaacacg | 780 |
| agagttcaaa tgacctggag ttaccctgat gaaaaaaata gagagcttc cgtaaggcga | 840 |
| cgaattgacc aaagcaattc ccatgccaac atattctaca gtgttcttac tattgacaaa | 900 |
| atgcagaaca agacaaagg actttatact tgtcgtgtaa ggagtggacc atcattcaaa | 960 |
| tctgttaaca cctcagtgca tatatatgat aaagcattca tcactgtgaa acatcgaaaa | 1020 |
| cagcaggtgc ttgaaaccgt agctggcaag cggtcttacc ggctctctat gaaagtgaag | 1080 |
| gcatttccct cgccggaagt tgtatggtta aagatgggt tacctgcgac tgagaaatct | 1140 |
| gctcgctatt tgactcgtgg ctactcgtta attatcaagg acgtaactga agaggatgca | 1200 |
| gggaattata caatcttgct gagcataaaa cagtcaaatg tgtttaaaaa cctcactgcc | 1260 |
| actctaattg tcaatgtgaa acccagatt tacgaaaagg ccgtgtcatc gtttccagac | 1320 |
| ccggctctct acccactggg cagcagacaa atcctgactt gtaccgcata tggtatccct | 1380 |
| caacctacaa tcaagtggtt ctggcacccc tgtaaccata tcattccga agcaaggtgt | 1440 |
| gactttgttt ccaataatga agagtccttt atcctggatg ctgacagcaa catgggaaac | 1500 |
| agaattgaga gcatcactca gcgcatggca ataatagaag gaaagaataa gatggctagc | 1560 |

```
accttggttg tggctgactc tagaatttct ggaatctaca tttgcatagc ttccaataaa   1620
gttgggactg tgggaagaaa cataagcttt tatatcacag atgtgccaaa tgggtttcat   1680
gttaacttgg aaaaaatgcc gacggaagga gaggacctga aactgtcttg cacagttaac   1740
aagttcttat acagagacgt tacttggatt ttactgcgga cagttaataa cagaacaatg   1800
cactacagta ttagcaagca aaaaatggcc atcactaagg agcactccat cactcttaat   1860
cttaccatca tgaatgtttc cctgcaagat tcaggcacct atgcctgcag agccaggaat   1920
gtatacacag gggaagaaat cctccagaag aaagaaatta caatcagaga tcaggaagca   1980
ccatacctcc tgcgaaacct cagtgatcac acagtggcca tcagcagttc caccactta   2040 gactgtcatg ctaatggtgt ccccgagcct cagatcactt ggtttaaaaa caaccacaaa   2100
atacaacaag agcctggaat tattttagga ccaggaagca gcacgctgtt tattgaagga   2160
gtcacagaag aggatgaagg tgtctatcac tgcaaagcca ccaaccagaa gggctctgtg   2220
gaaagttcag catacctcac tgttcaagga acctcggaca gtctaatct ggagctgatc   2280 actctaacat gcacctgtgt ggctgcgact ctcttctggc tcctattaac cctctttatc   2340
cgaaaaatga aaaggtcttc ttctgaaata aagactgact acctatcaat tataatggac   2400
ccagatgaag ttcctttgga tgagcagtgt gagcggctcc cttatgatgc cagcaagtgg   2460
gagtttgccc gggagagact taaactgggc aaatcacttg aagaggggc ttttggaaaa   2520 gtggttcaag catcagcatt tggcattaag aaatcaccta cgtgccggac tgtggctgtg   2580
aaaatgctga agagggggc cacggccagc gagtacaaag ctctgatgac tgagctaaaa   2640
atcttgaccc acattggcca ccatctgaac gtggttaacc tgctgggagc ctgcaccaag   2700
caaggagggc tctgatggt gattgttgaa tactgcaaat atggaaatct ctccaactac   2760
ctcaagagca acgtgactt attttttctc aacaaggatg cagcactaca catggagcct   2820
aagaaagaaa aaatggagcc aggcctggaa caagcaaga aaccaagact agatagcgtc   2880
accagcagcg aaagctttgc gagctccggc tttcaggaag ataaaagtct gagtgatgtt   2940
gaggaagagg aggattctga cggttttctac aaggagccca tcactatgga agatctgatt   3000
tcttacagtt ttcaagtggc cagaggcatg gagttcctgt cttccagaaa gtgcattcat   3060
cgggacctgg cagcgagaaa cattctttta tctgagaaca cgtggtgaa gatttgtgat   3120 tttggccttg cccgggatat ttataagaac cccgattatg tgagaaaagg agatactcga   3180
cttcctctga aatggatggc tcctgaatct atctttgaca aaatctacag caccaagagc   3240
gacgtgtggt cttacggagt attgctgtgg gaaatcttct ccttaggtgg gtctccatac   3300
ccaggagtac aaatggatga ggacttttgc agtcgcctga gggaaggcat gaggatgaga   3360
gctcctgagt actctactcc tgaaatctat cagatcatgc tggactgctg gcacagagac   3420
ccaaaagaaa ggccaagatt tgcagaactt gtggaaaaac taggtgattt gcttcaagca   3480
aatgtacaac aggatggtaa agactacatc ccaatcaatg ccatactgac aggaaatagt   3540
gggtttacat actcaactcc tgccttctct gaggacttct tcaaggaaag tatttcagct   3600 ccgaagtta attcaggaag ctctgatgat gtcagatatg taaatgcttt caagttcatg   3660
agcctggaaa gaatcaaaac ctttgaagaa ctttaccga atgccacctc catgtttgat   3720
gactaccagg cgacagcag cactctgttg gcctctccca tgctgaagcg cttcacctgg   3780
actgacagca aacccaaggc ctcgctcaag attgacttga gagtaaccag taaaagtaag   3840
gagtcggggc tgtctgatgt cagcaggccc agtttctgcc attccagctg tgggcacgtc   3900
```

-continued

```
agcgaaggca agcgcaggtt cacctacgac cacgctgagc tggaaaggaa aatcgcgtgc   3960
tgctccccgc ccccagacta caactcggtg gtcctgtact ccaccccacc catctag      4017
```

<210> SEQ ID NO 4
<211> LENGTH: 1338
<212> TYPE: PRT
<213> ORGANISM: human

<400> SEQUENCE: 4

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365
```

-continued

```
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                    405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                    485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
        530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                    565                 570                 575
Cys Thr Val Asn Lys Phe Leu Tyr Arg Asp Val Thr Trp Ile Leu Leu
                580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
        610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                    645                 650                 655
Asp Gln Glu Ala Pro Tyr Leu Leu Arg Asn Leu Ser Asp His Thr Val
                660                 665                 670
Ala Ile Ser Ser Ser Thr Thr Leu Asp Cys His Ala Asn Gly Val Pro
            675                 680                 685
Glu Pro Gln Ile Thr Trp Phe Lys Asn Asn His Lys Ile Gln Gln Glu
        690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                    725                 730                 735
Lys Gly Ser Val Glu Ser Ser Ala Tyr Leu Thr Val Gln Gly Thr Ser
                740                 745                 750
Asp Lys Ser Asn Leu Glu Leu Ile Thr Leu Thr Cys Thr Cys Val Ala
            755                 760                 765
Ala Thr Leu Phe Trp Leu Leu Leu Thr Leu Phe Ile Arg Lys Met Lys
        770                 775                 780
Arg Ser Ser Ser Glu Ile Lys Thr Asp Tyr Leu Ser Ile Ile Met Asp
785                 790                 795                 800
```

-continued

```
Pro Asp Glu Val Pro Leu Asp Glu Gln Cys Glu Arg Leu Pro Tyr Asp
            805                 810                 815
Ala Ser Lys Trp Glu Phe Ala Arg Glu Arg Leu Lys Leu Gly Lys Ser
            820                 825                 830
Leu Gly Arg Gly Ala Phe Gly Lys Val Val Gln Ala Ser Ala Phe Gly
            835                 840                 845
Ile Lys Lys Ser Pro Thr Cys Arg Thr Val Ala Val Lys Met Leu Lys
    850                 855                 860
Glu Gly Ala Thr Ala Ser Glu Tyr Lys Ala Leu Met Thr Glu Leu Lys
865                 870                 875                 880
Ile Leu Thr His Ile Gly His His Leu Asn Val Val Asn Leu Leu Gly
            885                 890                 895
Ala Cys Thr Lys Gln Gly Gly Pro Leu Met Val Ile Val Glu Tyr Cys
            900                 905                 910
Lys Tyr Gly Asn Leu Ser Asn Tyr Leu Lys Ser Lys Arg Asp Leu Phe
            915                 920                 925
Phe Leu Asn Lys Asp Ala Ala Leu His Met Glu Pro Lys Lys Glu Lys
            930                 935                 940
Met Glu Pro Gly Leu Glu Gln Gly Lys Lys Pro Arg Leu Asp Ser Val
945                 950                 955                 960
Thr Ser Ser Glu Ser Phe Ala Ser Ser Gly Phe Gln Glu Asp Lys Ser
            965                 970                 975
Leu Ser Asp Val Glu Glu Glu Asp Ser Asp Gly Phe Tyr Lys Glu
            980                 985                 990
Pro Ile Thr Met Glu Asp Leu Ile Ser Tyr Ser Phe Gln Val Ala Arg
            995                1000                1005
Gly Met Glu Phe Leu Ser Ser Arg Lys Cys Ile His Arg Asp Leu Ala
    1010                1015                1020
Ala Arg Asn Ile Leu Leu Ser Glu Asn Asn Val Val Lys Ile Cys Asp
1025                1030                1035                1040
Phe Gly Leu Ala Arg Asp Ile Tyr Lys Asn Pro Asp Tyr Val Arg Lys
            1045                1050                1055
Gly Asp Thr Arg Leu Pro Leu Lys Trp Met Ala Pro Glu Ser Ile Phe
            1060                1065                1070
Asp Lys Ile Tyr Ser Thr Lys Ser Asp Val Trp Ser Tyr Gly Val Leu
            1075                1080                1085
Leu Trp Glu Ile Phe Ser Leu Gly Gly Ser Pro Tyr Pro Gly Val Gln
            1090                1095                1100
Met Asp Glu Asp Phe Cys Ser Arg Leu Arg Glu Gly Met Arg Met Arg
1105                1110                1115                1120
Ala Pro Glu Tyr Ser Thr Pro Glu Ile Tyr Gln Ile Met Leu Asp Cys
            1125                1130                1135
Trp His Arg Asp Pro Lys Glu Arg Pro Arg Phe Ala Glu Leu Val Glu
            1140                1145                1150
Lys Leu Gly Asp Leu Leu Gln Ala Asn Val Gln Gln Asp Gly Lys Asp
            1155                1160                1165
Tyr Ile Pro Ile Asn Ala Ile Leu Thr Gly Asn Ser Gly Phe Thr Tyr
            1170                1175                1180
Ser Thr Pro Ala Phe Ser Glu Asp Phe Phe Lys Glu Ser Ile Ser Ala
1185                1190                1195                1200
Pro Lys Phe Asn Ser Gly Ser Ser Asp Asp Val Arg Tyr Val Asn Ala
            1205                1210                1215
Phe Lys Phe Met Ser Leu Glu Arg Ile Lys Thr Phe Glu Glu Leu Leu
            1220                1225                1230
```

```
Pro Asn Ala Thr Ser Met Phe Asp Asp Tyr Gln Gly Asp Ser Ser Thr
        1235                1240                1245

Leu Leu Ala Ser Pro Met Leu Lys Arg Phe Thr Trp Thr Asp Ser Lys
    1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
            1285                1290                1295

Cys Gly His Val Ser Glu Gly Lys Arg Arg Phe Thr Tyr Asp His Ala
        1300                1305                1310

Glu Leu Glu Arg Lys Ile Ala Cys Cys Ser Pro Pro Asp Tyr Asn
        1315                1320                1325

Ser Val Val Leu Tyr Ser Thr Pro Pro Ile
        1330                1335

<210> SEQ ID NO 5
<211> LENGTH: 5390
<212> TYPE: DNA
<213> ORGANISM: mouse

<400> SEQUENCE: 5
ctgtgtcccg cagccggata acctggctga cccgattccg cggacaccgc tgcagccgcg     60
gctggagcca gggcgccggt gccccgcgct ctccccggtc ttgcgctgcg ggggccatac    120
cgcctctgtg acttctttgc gggccaggga cggagaagga gtctgtgcct gagaaactgg    180
gctctgtgcc caggcgcgag gtgcaggatg gagagcaagg cgctgctagc tgtcgctctg    240
tggttctgcg tggagacccg agccgcctct gtgggtttga ctggcgattt tctccatccc    300
cccaagctca gcacacagaa agacatactg acaattttgg caaatacaac ccttcagatt    360
acttgcaggg gacagcggga cctggactgg cttttggccca atgctcagcg tgattctgag    420
gaaagggtat tggtgactga atgcggcggt ggtgacagta tcttctgcaa aacactcacc    480
attcccaggg tggttggaaa tgatactgga gcctacaagt gctcgtaccg ggacgtcgac    540
atagcctcca ctgtttatgt ctatgttcga gattacagat caccattcat cgcctctgtc    600
agtgaccagc atggcatcgt gtacatcacc gagaacaaga caaaactgt ggtgatcccc    660 tgccgagggt cgatttcaaa cctcaatgtg tctctttgcg ctaggtatcc agaaaagaga    720
tttgttccgg atggaaacag aatttcctgg gacagcgaga taggctttac tctccccagt    780
tacatgatca gctatgccgg catggtcttc tgtgaggcaa agatcaatga tgaaacctat    840
cagtctatca tgtacatagt tgtggttgta ggatatagga tttatgatgt gattctgagc    900
cccccgcatg aaattgagct atctgccgga gaaaaacttg tcttaaattg tacagcgaga    960
acagagctca atgtggggct tgatttcacc tggcactctc caccttcaaa gtctcatcat   1020
aagaagattg taaaccggga tgtgaaaccc tttcctggga ctgtggcgaa gatgtttttg   1080
agcaccttga caatagaaag tgtgaccaag agtgaccaag gggaatacac ctgtgtagcg   1140
tccagtggac ggatgatcaa gagaaataga acatttgtcc gagttcacac aaagccttt   1200 attgcttcg gtagtgggat gaaatctttg gtggaagcca cagtgggcag tcaagtccga   1260
atccctgtga agtatctcag ttacccagct cctgatatca aatggtacag aaatggaagg   1320
cccattgagt ccaactacac aatgattgtt ggcgatgaac tcaccatcat ggaagtgact   1380
gaaagagatg caggaaacta cacggtcatc ctcaccaacc ccatttcaat ggagaaacag   1440
agccacatgg tctctctggt tgtgaatgtc ccaccccaga tcgtgagaa agccttgatc   1500 tcgcctatgg attcctacca gtatgggacc atgcagacat tgacatgcac agtctacgcc   1560
```

```
aaccctcccc tgcaccacat ccagtggtac tggcagctag aagaagcctg ctcctacaga   1620
cccggccaaa caagcccgta tgcttgtaaa gaatggagac acgtggagga tttccagggg   1680
ggaaacaaga tcgaagtcac caaaaaccaa tatgccctga ttgaaggaaa aaacaaaact   1740
gtaagtacgc tggtcatcca agctgccaac gtgtcagcgt tgtacaaatg tgaagccatc   1800
aacaaagcgg gacgaggaga gagggtcatc tccttccatg tgatcagggg tcctgaaatt   1860
actgtgcaac ctgctgccca gccaactgag caggagagtg tgtccctgtt gtgcactgca   1920
gacagaaata cgtttgagaa cctcacgtgg tacaagcttg gctcacaggc aacatcggtc   1980
cacatgggcg aatcactcac accagtttgc aagaacttgg atgctctttg gaaactgaat   2040
ggcaccatgt tttctaacag cacaaatgac atcttgattg tggcatttca gaatgcctct   2100
ctgcaggacc aaggcgacta tgtttgctct gctcaagata agaagaccaa gaaaagacat   2160
tgcctggtca acagctcat catcctagag cgcatggcac ccatgatcac cggaaatctg   2220
gagaatcaga caacaaccat tggcgagacc attgaagtga cttgcccagc atctggaaat   2280
cctaccccac acattacatg gttcaaagac aacgagaccc tggtagaaga ttcaggcatt   2340
gtactgagag atgggaaccg gaacctgact atccgcaggg tgaggaagga ggatggaggc   2400
ctctacacct gccaggcctg caatgtcctt ggctgtgcaa gagcggagac gctcttcata   2460
atagaaggtg cccaggaaaa gaccaacttg gaagtcatta tcctcgtcgg cactgcagtg   2520
attgccatgt tcttctggct ccttcttgtc attgtcctac ggaccgttaa gcgggccaat   2580
gaaggggaac tgaagacagg ctacttgtct attgtcatgg atccagatga attgcccttg   2640
gatgagcgct gtgaacgctt gccttatgat gccagcaagt gggaattccc cagggaccgg   2700
ctgaaactag gaaaacctct tggccgcggt gccttcggcc aagtgattga ggcagacgct   2760
tttggaattg acaagacagc gacttgcaaa acagtagccg tcaagatgtt gaaagaagga   2820
gcaacacaca gcgagcatcg agccctcatg tctgaactca agatcctcat ccacattggt   2880
caccatctca atgtggtgaa cctcctaggc gcctgcacca agccgggagg gcctctcatg   2940
gtgattgtgg aattctgcaa gtttggaaac ctatcaactt acttacgggg caagagaaat   3000
gaatttgttc cctataagag caaggggca cgcttccgcc agggcaagga ctacgttggg   3060
gagctctccg tggatctgaa aagacgcttg gacagcatca ccagcagcca gagctctgcc   3120
agctcaggct tgttgagga gaaatcgctc agtgatgtag aggaagaaga agcttctgaa   3180
gaactgtaca aggacttcct gaccttggag catctcatct gttacagctt ccaagtggct   3240
aagggcatgg agttcttggc atcaaggaag tgtatccaca gggacctggc agcacgaaac   3300
attctcctat cggagaagaa tgtggttaag atctgtgact tcggcttggc ccgggacatt   3360
tataaagacc cggattatgt cagaaaagga gatgcccgac tcccctttga gtggatggcc   3420
ccggaaacca ttttttgacag agtatacaca attcagagcg atgtgtggtc tttcggtgtg   3480
ttgctctggg aaatatttc cttaggtgcc tccccatacc ctgggggtcaa gattgatgaa   3540 gaattttgta ggagattgaa agaaggaact agaatgcggg ctcctgacta cactacccca   3600
gaaatgtacc agaccatgct ggactgctgg catgaggacc ccaaccagag accctcgttt   3660
tcagagttgg tggagcattt gggaaacctc ctgcaagcaa atgcgcagca ggatggcaaa   3720
gactatattg ttcttccaat gtcagagaca ctgagcatgg aagaggattc tggactctcc   3780
ctgcctacct cacctgtttc ctgtatggag gaagaggaag tgtgcgaccc caaattccat   3840
tatgacaaca cagcaggaat cagtcattat ctccagaaca gtaagcgaaa gagccggcca   3900
gtgagtgtaa aaacatttga agatatccca ttggaggaac cagaagtaaa agtgatccca   3960
```

-continued

```
gatgacagcc agacagacag tgggatggtc cttgcatcag aagagctgaa aactctggaa    4020
gacaggaaca aattatctcc atcttttggt ggaatgatgc ccagtaaaag cagggagtct    4080
gtggcctcgg aaggctccaa ccagaccagt ggctaccagt ctgggtatca ctcagatgac    4140
acagacacca ccgtgtactc cagcgacgag gcaggacttt aaagatggt ggatgctgca     4200
gttcacgctg actcagggac cacactgcgc tcacctcctg tttaaatgga agtggtcctg    4260
tcccggctcc gcccccaact cctggaaatc acgagagagg tgctgcttag attttcaagt   4320
gttgttcttt ccaccacccg gaagtagcca catttgattt tcattttgg aggagggacc    4380
tcagactgca aggagcttgt cctcagggca tttccagaga agatgcccat gacccaagaa   4440
tgtgttgact ctactctctt ttccattcat ttaaaagtcc tatataatgt gccctgctgt   4500
ggtctcacta ccagttaaag caaaagactt tcaaacacgt ggactctgtc ctccaagaag  4560
tggcaacggc acctctgtga aactggatcg aatgggcaat gctttgtgtg ttgaggatgg   4620
gtgagatgtc ccagggccga gtctgtctac cttggaggct ttgtggagga tgcggctatg   4680
agccaagtgt taagtgtggg atgtggactg ggaggaagga aggcgcaagt cgctcggaga   4740
gcggttggag cctgcagatg cattgtgctg gctctggtgg aggtgggctt gtggcctgtc   4800
aggaaacgca aaggcggccg gcagggtttg gttttggaag gtttgcgtgc tcttcacagt   4860
cgggttacag gcgagttccc tgtggcgttt cctactccta atgagagttc cttccggact   4920
cttacgtgtc tcctggcctg gccccaggaa ggaaatgatg cagcttgctc cttcctcatc   4980
tctcaggctg tgccttaatt cagaacacca aagagagga acgtcggcag aggtccctga   5040
cggggccgaa gaattgtgag aacagaacag aaactcaggg tttctgctgg gtggagaccc   5100
acgtggcgcc ctggtggcag gtctgagggt tctctgtcaa gtggcggtaa aggctcaggc   5160
tggtgttctt cctctatctc cactcctgtc aggccccca gtcctcagta ttttagcttt    5220
gtggcttcct gatggcagaa aaatcttaat tggttggttt gctctccaga taatcactag   5280
ccagatttcg aaattacttt ttagccgagg ttatgataac atctactgta tcctttagaa   5340
ttttaaccta taaaactatg tctactggtt tctgcctgtg tgcttatgtt                5390
```

<210> SEQ ID NO 6
<211> LENGTH: 1345
<212> TYPE: PRT
<213> ORGANISM: mouse

<400> SEQUENCE: 6

```
Met Glu Ser Lys Ala Leu Leu Ala Val Ala Leu Trp Phe Cys Val Glu
  1               5                  10                  15

Thr Arg Ala Ala Ser Val Gly Leu Thr Gly Asp Phe Leu His Pro Pro
                 20                  25                  30

Lys Leu Ser Thr Gln Lys Asp Ile Leu Thr Ile Leu Ala Asn Thr Thr
             35                  40                  45

Leu Gln Ile Thr Cys Arg Gly Gln Arg Asp Leu Asp Trp Leu Trp Pro
         50                  55                  60

Asn Ala Gln Arg Asp Ser Glu Glu Arg Val Leu Val Thr Glu Cys Gly
     65                  70                  75                  80

Gly Gly Asp Ser Ile Phe Cys Lys Thr Leu Thr Ile Pro Arg Val Val
                 85                  90                  95

Gly Asn Asp Thr Gly Ala Tyr Lys Cys Ser Tyr Arg Asp Val Asp Ile
                100                 105                 110

Ala Ser Thr Val Tyr Val Tyr Val Arg Asp Tyr Arg Ser Pro Phe Ile
            115                 120                 125
```

-continued

```
Ala Ser Val Ser Asp Gln His Gly Ile Val Tyr Ile Thr Glu Asn Lys
        130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
            165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
        210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
            245                 250                 255

Gly Leu Asp Phe Thr Trp His Ser Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
            325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
            355                 360                 365

Asn Gly Arg Pro Ile Glu Ser Asn Tyr Thr Met Ile Val Gly Asp Glu
            370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
            435                 440                 445

Val Tyr Ala Asn Pro Pro Leu His His Ile Gln Trp Tyr Trp Gln Leu
450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
530                 535                 540

Val Ile Arg Gly Pro Glu Ile Thr Val Gln Pro Ala Ala Gln Pro Thr
545                 550                 555                 560
```

-continued

```
Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
    690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Val Leu
    770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
        835                 840                 845

Ala Asp Ala Phe Gly Ile Asp Lys Thr Ala Thr Cys Lys Thr Val Ala
    850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Cys Lys Phe Gly Asn Leu Ser Thr Tyr Leu Arg Gly
        915                 920                 925

Lys Arg Asn Glu Phe Val Pro Tyr Lys Ser Lys Gly Ala Arg Phe Arg
    930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
                965                 970                 975

Glu Glu Lys Ser Leu Ser Asp Val Glu Glu Glu Glu Ala Ser Glu Glu
            980                 985                 990
```

Leu Tyr Lys Asp Phe Leu Thr Leu Glu His Leu Ile Cys Tyr Ser Phe
        995                 1000                1005

Gln Val Ala Lys Gly Met Glu Phe Leu Ala Ser Arg Lys Cys Ile His
    1010                1015                1020

Arg Asp Leu Ala Ala Arg Asn Ile Leu Leu Ser Glu Lys Asn Val Val
1025                1030                1035                1040

Lys Ile Cys Asp Phe Gly Leu Ala Arg Asp Ile Tyr Lys Asp Pro Asp
        1045                1050                1055

Tyr Val Arg Lys Gly Asp Ala Arg Leu Pro Leu Lys Trp Met Ala Pro
            1060                1065                1070

Glu Thr Ile Phe Asp Arg Val Tyr Thr Ile Gln Ser Asp Val Trp Ser
        1075                1080                1085

Phe Gly Val Leu Leu Trp Glu Ile Phe Ser Leu Gly Ala Ser Pro Tyr
    1090                1095                1100

Pro Gly Val Lys Ile Asp Glu Glu Phe Cys Arg Arg Leu Lys Glu Gly
1105                1110                1115                1120

Thr Arg Met Arg Ala Pro Asp Tyr Thr Thr Pro Glu Met Tyr Gln Thr
            1125                1130                1135

Met Leu Asp Cys Trp His Glu Asp Pro Asn Gln Arg Pro Ser Phe Ser
        1140                1145                1150

Glu Leu Val Glu His Leu Gly Asn Leu Leu Gln Ala Asn Ala Gln Gln
    1155                1160                1165

Asp Gly Lys Asp Tyr Ile Val Leu Pro Met Ser Glu Thr Leu Ser Met
1170                1175                1180

Glu Glu Asp Ser Gly Leu Ser Leu Pro Thr Ser Pro Val Ser Cys Met
1185                1190                1195                1200

Glu Glu Glu Glu Val Cys Asp Pro Lys Phe His Tyr Asp Asn Thr Ala
            1205                1210                1215

Gly Ile Ser His Tyr Leu Gln Asn Ser Lys Arg Lys Ser Arg Pro Val
        1220                1225                1230

Ser Val Lys Thr Phe Glu Asp Ile Pro Leu Glu Glu Pro Glu Val Lys
    1235                1240                1245

Val Ile Pro Asp Asp Ser Gln Thr Asp Ser Gly Met Val Leu Ala Ser
    1250                1255                1260

Glu Glu Leu Lys Thr Leu Glu Asp Arg Asn Lys Leu Ser Pro Ser Phe
1265                1270                1275                1280

Gly Gly Met Met Pro Ser Lys Ser Arg Glu Ser Val Ala Ser Glu Gly
            1285                1290                1295

Ser Asn Gln Thr Ser Gly Tyr Gln Ser Gly Tyr His Ser Asp Asp Thr
        1300                1305                1310

Asp Thr Thr Val Tyr Ser Ser Asp Glu Ala Gly Leu Leu Lys Met Val
    1315                1320                1325

Asp Ala Ala Val His Ala Asp Ser Gly Thr Thr Leu Arg Ser Pro Pro
    1330                1335                1340

Val
1345

<210> SEQ ID NO 7
<211> LENGTH: 9
<212> TYPE: PRT
<213> ORGANISM: Mus musculus

<400> SEQUENCE: 7

Arg Gly Gln Arg Asp Leu Asp Trp Leu
 1               5

<210> SEQ ID NO 8
<211> LENGTH: 9
<212> TYPE: PRT
<213> ORGANISM: Mus musculus

<400> SEQUENCE: 8

Thr Tyr Gln Ser Ile Met Tyr Ile Val
1               5

<210> SEQ ID NO 9
<211> LENGTH: 9
<212> TYPE: PRT
<213> ORGANISM: Mus musculus

<400> SEQUENCE: 9

Val Gly Tyr Arg Ile Tyr Asp Val Ile
1               5

<210> SEQ ID NO 10
<211> LENGTH: 9
<212> TYPE: PRT
<213> ORGANISM: Mus musculus

<400> SEQUENCE: 10

Trp Tyr Arg Asn Gly Arg Pro Ile Glu
1               5

<210> SEQ ID NO 11
<211> LENGTH: 9
<212> TYPE: PRT
<213> ORGANISM: Mus musculus

<400> SEQUENCE: 11

Gln Tyr Gly Thr Met Gln Thr Leu Thr
1               5

<210> SEQ ID NO 12
<211> LENGTH: 9
<212> TYPE: PRT
<213> ORGANISM: Mus musculus

<400> SEQUENCE: 12

Leu Gly Cys Ala Arg Ala Glu Thr Leu
1               5

<210> SEQ ID NO 13
<211> LENGTH: 9
<212> TYPE: PRT
<213> ORGANISM: Mus musculus

<400> SEQUENCE: 13

Glu Gly Glu Leu Lys Thr Gly Tyr Leu
1               5

<210> SEQ ID NO 14
<211> LENGTH: 9
<212> TYPE: PRT
<213> ORGANISM: Mus musculus

<400> SEQUENCE: 14

Leu Tyr Lys Asp Phe Leu Tyr Thr Glu
1               5

```
<210> SEQ ID NO 15
<211> LENGTH: 9
<212> TYPE: PRT
<213> ORGANISM: Mus musculus

<400> SEQUENCE: 15

Gln Arg Pro Ser Phe Ser Glu Leu Val
 1               5

<210> SEQ ID NO 16
<211> LENGTH: 9
<212> TYPE: PRT
<213> ORGANISM: Mus musculus

<400> SEQUENCE: 16

Glu Leu Val Glu His Leu Gly Asn Leu
 1               5

<210> SEQ ID NO 17
<211> LENGTH: 9
<212> TYPE: PRT
<213> ORGANISM: Artificial Sequence
<220> FEATURE:
<223> OTHER INFORMATION: HIVtat

<400> SEQUENCE: 17

Arg Lys Lys Arg Arg Gln Arg Arg Arg
 1               5

<210> SEQ ID NO 18
<211> LENGTH: 9
<212> TYPE: PRT
<213> ORGANISM: Mus musculus

<400> SEQUENCE: 18

Arg Val Val Gly Asn Asp Thr Gly Ala
 1               5

<210> SEQ ID NO 19
<211> LENGTH: 9
<212> TYPE: PRT
<213> ORGANISM: Mus musculus

<400> SEQUENCE: 19

Val Ile Leu Thr Asn Pro Ile Ser Met
 1               5

<210> SEQ ID NO 20
<211> LENGTH: 9
<212> TYPE: PRT
<213> ORGANISM: Mus musculus

<400> SEQUENCE: 20

Phe His Tyr Asp Asn Thr Ala Gly Ile
 1               5

<210> SEQ ID NO 21
<211> LENGTH: 9
<212> TYPE: PRT
<213> ORGANISM: Mus musculus

<400> SEQUENCE: 21

Arg Gly Gln Arg Asp Leu Asp Trp Leu
 1               5
```

```
<210> SEQ ID NO 22
<211> LENGTH: 9
<212> TYPE: PRT
<213> ORGANISM: Mus musculus

<400> SEQUENCE: 22

Val Ile Ala Met Phe Phe Trp Leu Leu
 1               5

<210> SEQ ID NO 23
<211> LENGTH: 10
<212> TYPE: PRT
<213> ORGANISM: Mus musculus

<400> SEQUENCE: 23

Thr Thr Pro Glu Met His Tyr Gln Thr Met
 1               5                  10
```